(12) United States Patent
Charvat et al.

(10) Patent No.: US 10,188,337 B1
(45) Date of Patent: Jan. 29, 2019

(54) AUTOMATED CORRELATION OF NEUROPSYCHIATRIC TEST DATA

(71) Applicant: Savonix, Inc., San Francisco, CA (US)

(72) Inventors: Mylea Marie Charvat, San Francisco, CA (US); Devin Seto, Novato, CA (US)

(73) Assignee: SAVONIX, INC., San Francisco, CA (US)

( * ) Notice: Subject to any disclaimer, the term of this patent is extended or adjusted under 35 U.S.C. 154(b) by 0 days.

(21) Appl. No.: 15/077,628

(22) Filed: Mar. 22, 2016

Related U.S. Application Data

(60) Provisional application No. 62/208,635, filed on Aug. 22, 2015.

(51) Int. Cl.
| | | |
|---|---|---|
| *G09B 23/28* | (2006.01) | |
| *G09B 19/00* | (2006.01) | |
| *A61B 5/16* | (2006.01) | |
| *G16H 10/20* | (2018.01) | |

(52) U.S. Cl.
CPC ............... *A61B 5/16* (2013.01); *G16H 10/20* (2018.01)

(58) Field of Classification Search
None
See application file for complete search history.

(56) References Cited

U.S. PATENT DOCUMENTS

| | | | | |
|---|---|---|---|---|
| 6,280,198 B1 * | 8/2001 | Calhoun | ................... | A61B 5/16 434/236 |
| 8,568,311 B2 * | 10/2013 | LaPlaca | ................... | A61B 5/16 128/920 |

(Continued)

OTHER PUBLICATIONS

Ben-Zeev, Dror, et al. "Feasibility, acceptability, and preliminary efficacy of a smartphone intervention for schizophrenia." Schizophrenia bulletin (2014): sbu033.*

(Continued)

*Primary Examiner* — Anna Skibinsky
(74) *Attorney, Agent, or Firm* — Hickman Palermo Becker Bingham LLP

(57) ABSTRACT

A data processing method comprises, under program control of test instructions programmed in a mobile computing device, generating and causing displaying on a display device of the mobile computing device, a prompt associated with a first task that tests a feature of a human cognitive domain; in conjunction with causing displaying the prompt, by the test instructions, reading a system clock of the mobile computing device and storing a first time stamp value indicating when the prompt was displayed; by the test instructions, obtaining input via the mobile computing device comprising a response to the prompt; in conjunction with obtaining the input, by the test instructions, reading the system clock of the mobile computing device and storing a second time stamp value indicating when the input comprising the response was detected; by the test instructions, repeating the generating and causing displaying, the obtaining, and the storing the first time stamp value and the second time stamp value, for a plurality of other prompts of the same test, task or trial to yield a plurality of test records that associate a plurality of different response values with a plurality of respective different time stamp values, and transmitting the plurality of different response values and the plurality of respective different time stamp values over a data communications network to a server computer that is programmed with test analysis instructions; by the test analysis instructions, based upon the plurality of different response values and the plurality of respective different time stamp values, determining a first result score value for the first task, applying a first weight value to the first result score value to yield a first weighted result score value, and combining one or more other different weighted result score values with the first weighted result score value to yield a cognitive domain score value; with the server computer, causing generating and displaying one or more different graphs of the features of the cognitive domain.

19 Claims, 12 Drawing Sheets

(56) References Cited

U.S. PATENT DOCUMENTS

| | | | | |
|---|---|---|---|---|
| 2011/0029870 | A1* | 2/2011 | May | G06Q 10/109 |
| | | | | 715/710 |
| 2014/0199670 | A1* | 7/2014 | Stack | G09B 7/00 |
| | | | | 434/236 |
| 2014/0249447 | A1* | 9/2014 | Sereno | A61B 5/6898 |
| | | | | 600/558 |
| 2015/0119731 | A1* | 4/2015 | Yasumura | A61B 5/168 |
| | | | | 600/504 |
| 2015/0179079 | A1* | 6/2015 | Rodriguez, Jr. | G09B 5/00 |
| | | | | 434/236 |
| 2015/0279227 | A1* | 10/2015 | Huber | G09B 7/02 |
| | | | | 434/353 |

OTHER PUBLICATIONS

Morris et al. "Mobile Therapy: Case Study Evaluations of a Cell Phone Application for Emotional Self-Awareness," Journal of medical Internet research, vol. 12 (2010) pp. 1-21.*

Lane et al. "A Survey of Mobile Phone Sensing," IEEE Communications magazine (2010) vol. 48, pp. 140-150.*

* cited by examiner

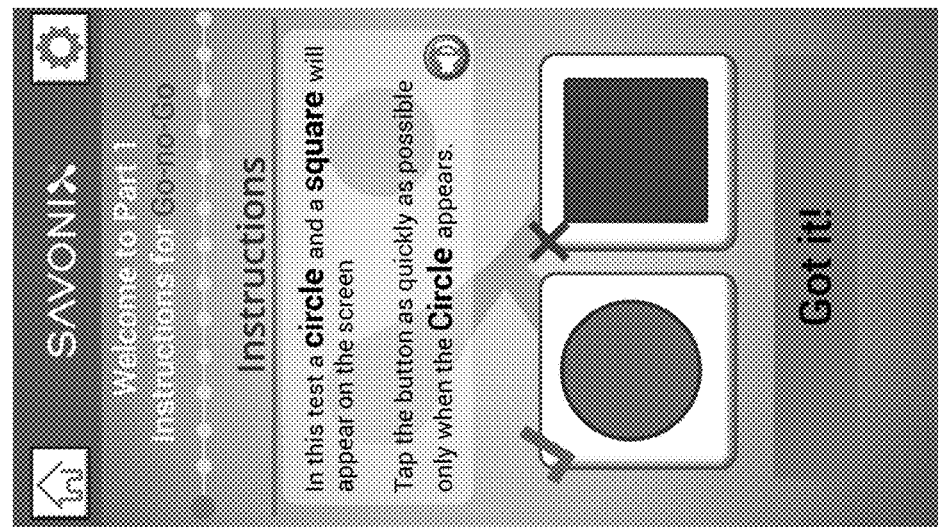
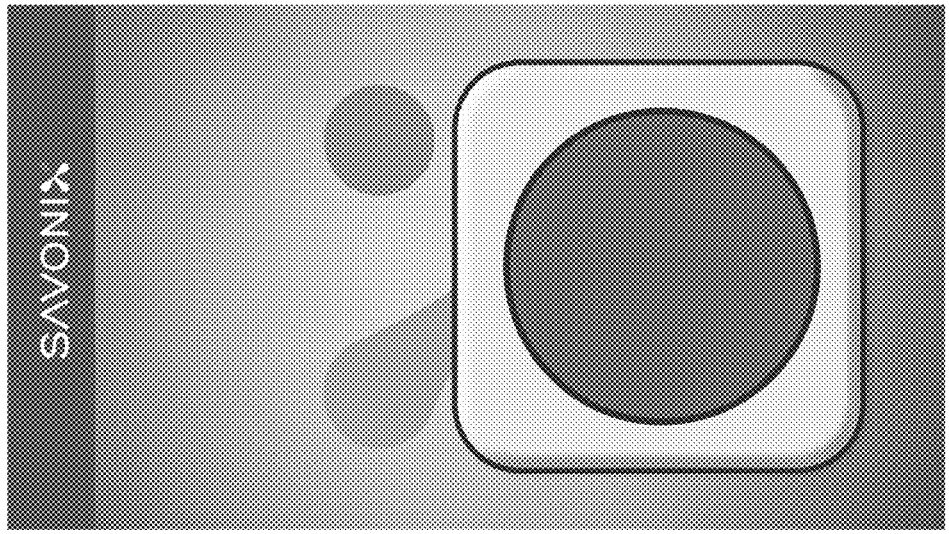
Fig. 4A
Fig. 4B

AUTOMATED CORRELATION OF NEUROPSYCHIATRIC TEST DATA

BENEFIT CLAIM

This application claims the benefit under 35 U.S.C. § 119(e) of provisional application 62/208,635, filed Aug. 22, 2015, the entire contents of which are hereby incorporated by reference for all purposes as if fully set forth herein.

FIELD OF THE DISCLOSURE

The present disclosure generally relates to computer-implemented measurement of responses to neuropsychiatric tests, compilation of test data, and automated analysis, scoring and interpretation of test data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Neuropsychiatric testing has been and continues to be administered using pen and paper, with some desktop computer augmented delivery. This approach is costly and subject to human error in scoring, particularly with regard to response time. It also requires a clinician to administer and deliver the tests, score the assessment and write up results that describe both rankings on the individual cognitive domains, such as attention or working memory, as well as produce an integrated report describing the overall results and how those results relate to real world function and abilities. Testing also may be subject to latent or explicit bias on the part of the clinician.

Existing computerized tests such as those from the United States National Institutes of Health (NIH) tool box are only available on desktop computers. They also require a clinician to explain, administer, interpret as well as write up the results and remain costly. Testing, scoring and report generation for emotional and cognitive function often run into the hundreds, if not thousands, of dollars per subject. When testing large numbers of subjects is needed, such as in the context of criminal justice systems, these costs are excessive in the aggregate.

SUMMARY OF THE INVENTION

The appended claims may serve as a summary of the invention.

BRIEF DESCRIPTION OF THE DRAWINGS

In the drawings:

FIG. 4A, FIG. 4B illustrate example computer screen displays that may be displayed as part of a GO NO GO test.

DETAILED DESCRIPTION

Figure 1:
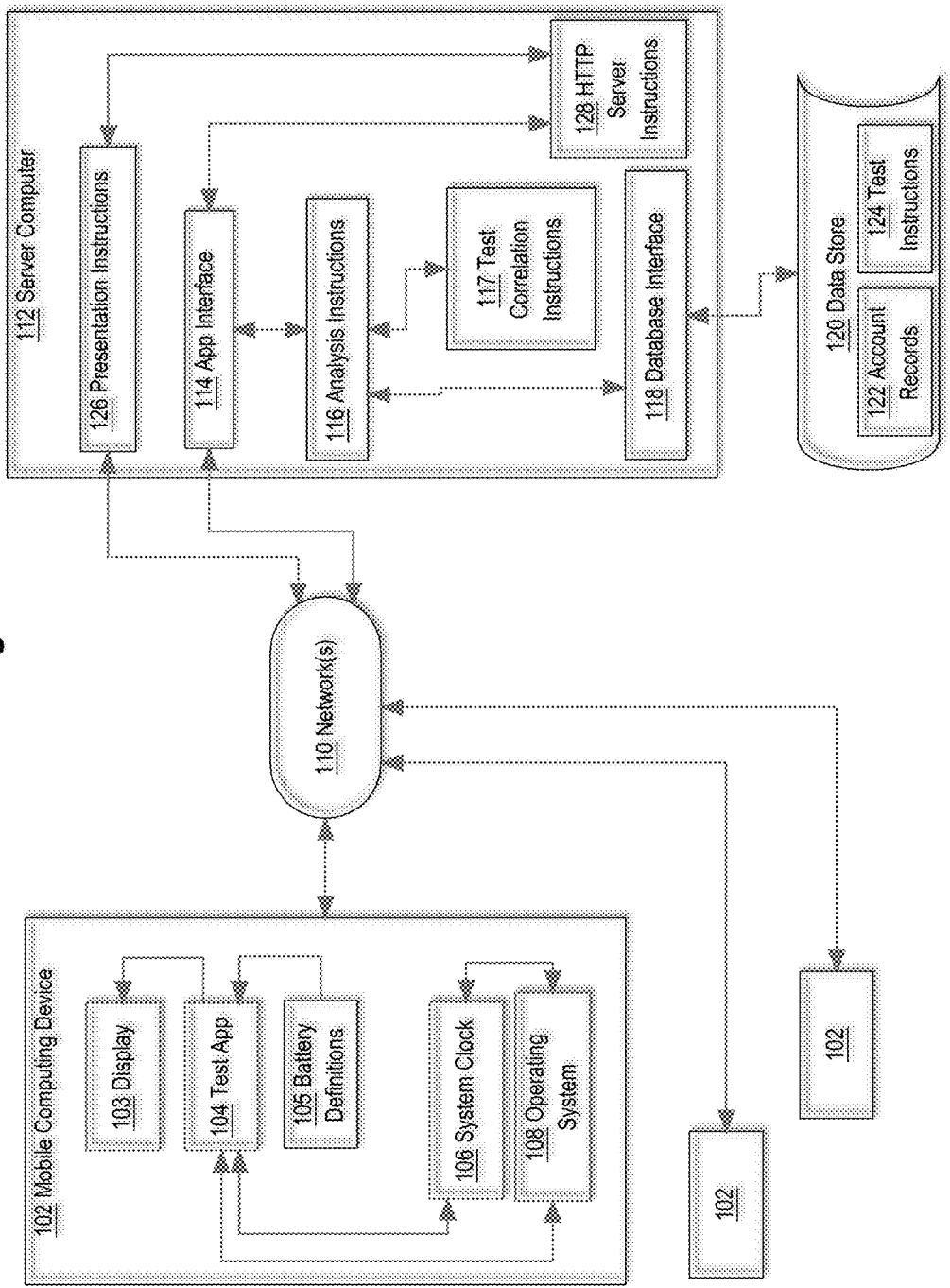
FIG. 1 illustrates a computer system with which embodiments may be implemented.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:
1. GENERAL OVERVIEW
2. STRUCTURAL OVERVIEW
3. FUNCTIONAL EXAMPLES
4. IMPLEMENTATION EXAMPLE—HARDWARE OVERVIEW

1. General Overview

In an embodiment, a data processing method comprises, under program control of test instructions programmed in a mobile computing device, generating and causing displaying on a display device of the mobile computing device, a prompt associated with a first task that tests a feature of a human cognitive domain; in conjunction with causing displaying the prompt, by the test instructions, reading a system clock of the mobile computing device and storing a first time stamp value indicating when the prompt was displayed; by the test instructions, obtaining input via the mobile computing device comprising a response to the prompt; in conjunction with obtaining the input, by the test instructions, reading the system clock of the mobile computing device and storing a second time stamp value indicating when the input comprising the response was detected; by the test instructions, repeating the generating and causing displaying, the obtaining, and the storing the first time stamp value and the second time stamp value, for a plurality of other prompts of the same test, task or trial to yield a plurality of test records that associate a plurality of different response values with a plurality of respective different time stamp values, and transmitting the plurality of different response values and the plurality of respective different time stamp values over a data communications network to a server computer that is programmed with test analysis instructions; by the test analysis instructions, based upon the plurality of different response values and the plurality of respective different time stamp values, determining a first result score value for the first task, applying a first weight value to the first result score value to yield a first weighted result score value, and combining one or more other different weighted result score values with the first weighted result score value to yield a cognitive domain score value; with the server computer, causing generating and displaying one or more different graphs of the features of the cognitive domain.

In some embodiments, a data processing method and system provides a computerized administration, scoring, and interpretation platform, executable using mobile computing devices, for a battery of valid, reliable tests for cognitive and emotional intelligence. Results from the tests are aggregated into a centralized dashboard that can be analyzed at either a group or individual level.

In some embodiments, a mobile computerized set of neuropsychiatric tests, delivers results for practitioners and individual users for areas of cognition including but not limited to negativity-positivity orientation, resilience, social skills, stress level, anxiety level, mood regulation, attention, cognitive flexibility, response inhibition, decision speed, executive function, information processing speed, working memory, psycho-motor coordination, verbal memory, emotion recognition, emotion processing rate, and reactive decision making.

In one embodiment, NeuroNet, a mobile computerized set of valid, reliable neurological tests, delivers results for EPP and individual users in the following areas of cognitive and emotional function: Negativity-Positivity Orientation, Resilience, Social Skills, Stress Level, Anxiety Level, Mood Regulation, Attention, Cognitive Flexibility, Response Inhibition, Decision Speed, Executive Function, Information Processing Speed, Working Memory, Psycho-motor Coordination, Verbal Memory, Emotion Recognition, Emotion Processing Rate, Reactive Decision Making. NeuroNet provides 100% mobile computerized administration, scoring, and testing of a standardized neuro-cognitive battery of tests. It provides results at the individual user level as well as at the enterprise level, allowing an employer or clinician a view of results across all users on their license.

2. Structural Overview

FIG. 1 illustrates a computer system with which embodiments may be implemented. In an embodiment, mobile computing devices 102 are communicatively coupled directly or indirectly via one or more networks 110 to a server computer 112. For purposes of illustrating a clear example, FIG. 1 shows three (3) instances of mobile computing devices 102 but practical embodiments may include any number including thousands or millions of such devices. Each mobile computing device 102 comprises a display 103, which may comprise a touch-sensitive screen, a test application or test app 104, battery definitions 105, system clock 106 and operating system 108. For clarity, other elements of mobile computing device 102 are omitted, such as a processor, I/O circuits, memory or other storage, wireless network interfaces, and optional I/O devices such as a loudspeaker, microphone input, keyboard and the like. In some embodiments, mobile computing devices 102 may comprise smartphones, tablet computers, laptop computers or other computers. Examples include APPLE IPHONE and IPAD devices, ANDROID smartphones, MICROSOFT SURFACE tablet computers, etc.

Test app 104 comprises stored sequences of executable instructions that implement the testing, reporting and correlation functions described herein, alone or in cooperation with server-side components of the server computer 112. In some embodiments, test app 104 may comprise an executable application program file that is downloadable from server computer 112 or another storage location. Examples include the APPLE APP STORE, GOOGLE PLAY store, etc. The battery definitions 105 comprises data stored in app memory or other storage that defines a plurality of neurological or neuropsychiatric tests to be administered to a subject. "Battery," in this context, refers to a set of two or more tests. Test app 104 is programmed to load battery definitions 105 upon startup, and the battery definitions then drive the test app to deliver two or more specific tests to the mobile computing device, to detect responses, and to store response data and/or transmit response data to the server computer 112.

System clock 106 continuously generates signals representing a current date and time, and can be queried programmatically either directly or by calling a service that is implemented as part of operating system 108.

The mobile computing devices 102 are coupled directly or indirectly via one or more networks 110 to server computer 112. Network 110 in FIG. 1 broadly represents any combination of one or more local area networks, wide area networks, campus networks, and internetworks using any of wired or wireless, terrestrial or satellite-based links.

In an embodiment, server computer 112 comprises an app interface 114, analysis instructions 116, test correlation instructions 117, and a database interface 118 that is communicatively coupled to a data store 120 having account records 122 and test instructions 124. The app interface 114 comprises instructions or logic that are programmed to send and receive messages, data, alerts and/or notifications to or from the test app 104 using a generalized programmatic application communication protocol, or app-specific communication mechanisms. Analysis instructions 116 comprises a set of executable instructions that are programmed to analyze, score and report on responses that are received from test app 104 via app interface 114, and may provide data to data store 120 or to a user terminal while the test app 104 is running, after a test is complete, after a battery is complete, or at other times.

In some embodiments, presentation instructions 126 coupled to HTTP server instructions 128 are programmed to receive requests of browser logic, using a standalone browser app at mobile computing device 102 or HTTP-compatible instructions in test app 104, or using a browser at another computer, and to respond with reply messages in HTTP that include HTML document content for dynamically generated web pages or other content. Using this approach, server computer 112 may implement a SaaS-based web application that an administrative user can use to perform functions that are further described herein, such as creating user records or account records 122 in data store 120, managing user records, forming test batteries or otherwise configuring test app 104, generating reports, inspecting data values such as responses and time stamps that have been captured during use of the test app 104 and transmitted to the server computer 112.

Test correlation instructions 117 comprise a set of executable instructions that are programmed to correlate the responses received from one particular test that was administered via test app 104 to the responses that were received based upon administering a different particular test. As described further below, test correlation instructions 117 may be programmed to interrelate response data from tests that are not ordinarily considered related, or to use response data from a first test in correlation with response data from a second test to generate different scores, reports or recommendations than those that might result from data from a single test.

Database interface 118 comprises a set of instructions that are programmed to mediate data read/write requests from the analysis instructions 116 in relation to the data store 120, which may comprise a relational database, non-relational database, object store, flat file system, or other data repository, in various embodiments. The organizational schema for tables or other units of data in data store 120 may vary in various embodiments. In one embodiment, data store 120 comprises account records 122 and test instructions 124, as seen in FIG. 1. Each of the account records 122 comprises a set of data relating to a particular user of the server computer and/or mobile computing device; for example, an account record may relate to a particular individual who uses one of the mobile computing devices to take tests. Test instructions 124 may comprise stored sets of executable instructions that can be updated into the test app 104 or retrieved as part of administering a particular test. Test instructions 124 also may broadly represent storage for copies or instances of the test app 104 for downloading to different mobile computing devices 102.

3. Functional Examples

Figure 2:
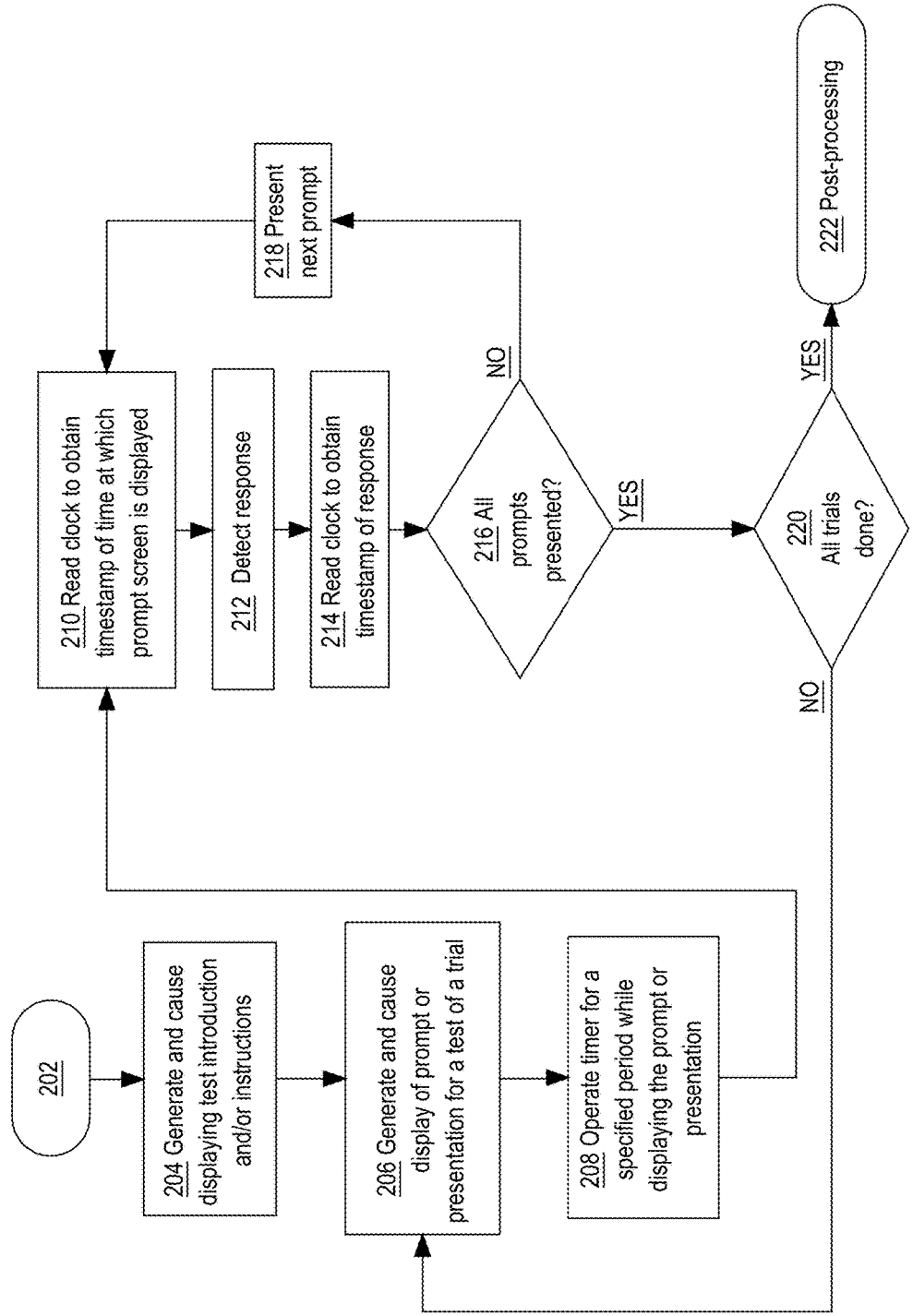
FIG. 2 illustrates a flow diagram of a process that may be used for computer-assisted neuropsychiatric testing with time recordation and cross-correlation to other tests.

FIG. 2 illustrates a flow diagram of a process that may be used for computer-assisted neuropsychiatric testing with time recordation and cross-correlation to other tests. FIG. 2, and each other flow diagram in the disclosure, represents an example of an algorithm that may be used as a basis for programming source code for the test app 104 and/or the test instructions 124, and then compiled, interpreted or otherwise transformed into one or more executable files for the test app 104 and/or the test instructions 124. Implementations may be programmed, for example, using any of JAVA, C, C++, OBJECTIVE-C, Pascal, assembler or any other human-readable source language that is convenient and then transformed using a compatible compiler, interpreter, or script processor. One or more source files may be programmed based on the algorithms herein and the test app 104 and test instructions 124 each may comprise one or more executables.

Block 202 represents a start of a particular test, which may include one or more trials. Block 202 may represent launching or initializing the execution of the test app 104 on a mobile computing device 102, or starting a battery of tests or starting a particular test within a battery of tests.

At block 204, the process generates and causes displaying a test introduction and/or instructions for a particular test. The introduction or instructions may be generated independently by the test app 104 and provided to a display of the mobile computing device 102, or obtained from the test instructions of the server computer. The introduction or instructions may comprise text, graphics, or video. In some embodiments, a countdown screen may be displayed on the screen of the mobile computing device 102 to prepare the user for the beginning of each individual test or step before it starts.

At block 206, the process generates and cause displaying a prompt or a presentation for a particular test of a particular trial. The prompt or presentation may consist of words, images, video, or other media. Other sections in this disclosure provide specific examples of particular prompts or presentations that may be used for particular kinds of tests. The process of FIG. 2 is generalized and applicable to all such tests.

At block 208, the process operates a timer within the test app 104 or other elements of the mobile computing device 102 for a specified period, while continuing to display the prompt or presentation. The timer may be implemented in software in the test app 104 or may be integrated with the system clock. In some embodiments, use of a timer is omitted. Not all tests require presenting the prompt of block 206 for a specified time as determined by a timer.

At block 210, the process obtains a timestamp of a time at which the prompt of block 206 was first displayed on the mobile computing device. For example, the process may read the system clock to obtain the timestamp. In an embodiment, the timestamp value obtained at block 210 is stored at least transiently, for example, in app storage of the test app 104, and/or transmitted to the server computer for storing in the data repository in association with records that identify the test, battery, mobile computing device 102, and/or a user account for a user of the mobile computing device.

At block 212, the process detects a response. Typically, block 212 involves detecting a tap, touch, gesture, or other event associated with a touch screen of the mobile computing device that resulted from the prompt of block 206. The response that is detected at block 212 may involve obtaining a user input event from the operating system of the mobile computing device 102, or obtaining a response detection programmatically through other means such as an interrupt handler. The particular mechanism is not critical and what is important is that the test app 104 obtains a programmatic signal when the mobile computing device 102 or its user provides a response to the prompt or presentation of block 206.

At block 214, the process obtains a timestamp of a time at which the response of block 212 occurred. For example, the process may read the system clock to obtain the timestamp. In an embodiment, the timestamp value obtained at block 214 is stored at least transiently, for example, in app storage of the test app 104, and/or transmitted to the server computer for storing in the data repository in association with records that identify the test, battery, mobile computing device 102, and/or a user account for a user of the mobile computing device.

Optionally, at or near block 214, the process computes a time difference value representing a difference between the time stamps of block 210, block 214, and thereby determines an elapsed time between displaying the prompt or presentation of block 206 and obtaining the response of block 212. The time difference value may be stored at least transiently, for example, in app storage of the test app 104, and/or transmitted to the server computer for storing in the data repository in association with records that identify the test, battery, mobile computing device 102, and/or a user account for a user of the mobile computing device. Or, in some embodiments, the time difference value may be computed by the server computer.

At block 216, the process tests whether all prompts have been presented for the current test. If not, then control transfers to block 218 to present the next prompt. Blocks 210, 212, 214, 216, 218 thus form a loop in which all prompts for a particular test are presented, responses are detected, and the process obtains and stores the times at which prompts are presented and responses are received.

At block 220, the process tests whether all trials have been presented for the current test. If not, then control transfers to block 206 to present the first prompt for the next trial of a test. Some tests may use two or more trials, and other tests may use a single trial.

If all trials of the current test have been presented, then control transfers to block 222 at which post-processing may be performed. In various embodiments, post-processing may involve: initiating execution of a next test in a particular battery; calculating, determining or generating a score, report, analysis or other results, locally with the test app 104 at the mobile computing device 102 or at the server computer; presenting the score, report, analysis or other results, locally with the test app 104 at the mobile computing device 102 or at the server computer. In some embodiments, generating a score, report or analysis comprises comparing the response time data that was obtained for particular prompts, trials or tests to the response time data, or other values, that are stored or have been obtained for other particular prompts, trials or tests. For example, the response data obtained for a first test may permit inferring traits, characteristics or properties about the mobile computing device 102, or the user account, based upon the response data that was obtained for a second test.

Figure 3:
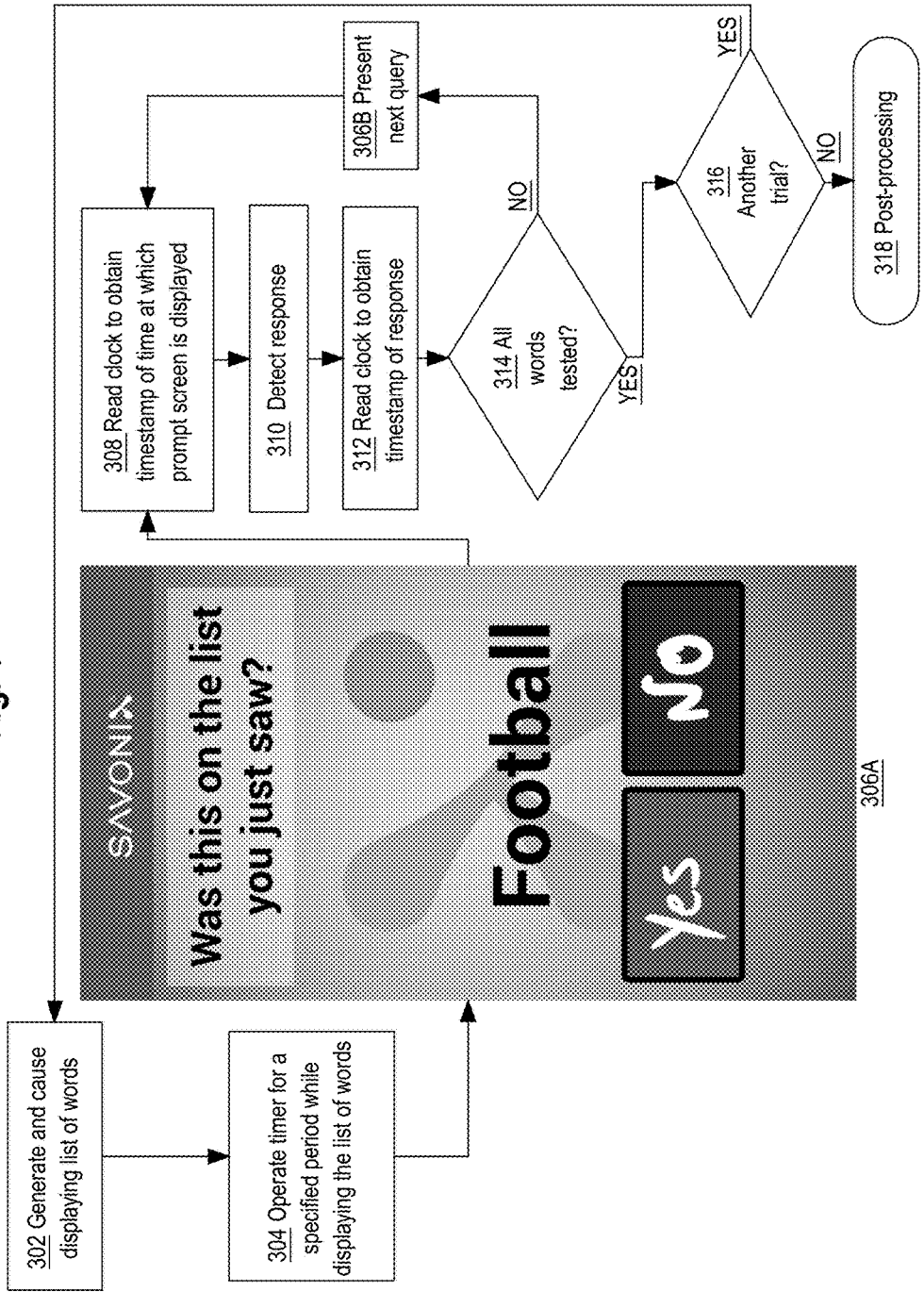
FIG. 3 is a flow diagram illustrating a process of administering a verbal learning test with integrated time stamp recording.

3.1 First Functional Example—Correlating Test Results Based Upon Computer-Detected Timestamp Data FIG. 3 is a flow diagram illustrating a process of administering a verbal learning test with integrated time stamp recording. In an embodiment, at block 302, the process generates and causes displaying a list of words. Displaying may comprise driving the display of the mobile computing device 102. In an embodiment, the display of the mobile computing device 102 is driven to display 12 words, optionally with a prompt or introduction screen that explains that the user of the mobile computing device is asked to memorize and recognize later from memory. As an example, the list contains 12 concrete words from a language known to the user; the words may be closely matched on concreteness, number of letters, and frequency.

At block 304, the process operates a timer for a specified period while displaying the list of the words. For example, the list might be presented for 20 seconds, and then control proceeds to a subsequent step in which a first query or prompt pertaining to a word is displayed; block 306A illustrates an example query display screen for a mobile computing device that prompts the user to touch YES or NO to indicate whether a particular word was on the previously presented list. At block 308, the process reads the system clock of the mobile computing device to obtain a time stamp at which the prompt screen 306A was first displayed.

At block 310, a response is detected. Typically, the response comprises a tap on a region of the display screen of the mobile computing device 102 consistent with selecting one of the displayed options such as YES or NO. Detecting a response may comprise programmatically receiving a TAP event from the operating system of the mobile computing device that contains sufficient coordinate data or the like to enable the test app 104 to determine whether YES or NO was selected in prompt screen 306A.

At block 312, the process obtains a timestamp at which the response of block 310 occurred. The timestamps of blocks 308, 312 may be stored in local app storage and/or may be transmitted via network messages to the server computer. In this manner the process of FIG. 3 may acquire or determine the precise elapsed time between presentation of a prompt screen 306A and receiving a response. When the system clock operates with millisecond precision, the timestamps of blocks 308, 312 may reflect user response time or reaction time to the millisecond.

At block 312, the process tests whether all words in the test have been presented to the user via the display of the mobile computing device. If not, then in block 306B a next query screen, similar to prompt screen 306A, is displayed, but with a different word, and control proceeds to block 308. Thus blocks 308-310-312-314-306B represent a loop that may be iterated one or more times up to a maximum number of times specified by a constant value or variable value. The number of words presented in this manner for testing may be the same as, or less than, the total number of words in the list.

At block 316, the process tests whether another trial should be performed. A trial, in this context, refers to presentation of a word list for a set period of time followed by prompting for words and recording YES/NO responses. If another trial is needed as specified by a stored constant value or a variable value, then control returns to block 302 to repeat the process for a different list of words. If no other trial is needed, then in block 318 post processing is performed, which may comprise determining scores or outcomes based upon the number of correct responses and/or the elapsed time per response, for particular word presentations, in the aggregate, or using mean values per word or other metrics based on time.

In one embodiment, the list is presented 4 times. In some embodiments, the list of words comprises single words. In another embodiment, the list of words comprises pairs of words in which one is a word to be tested and the second is a distractor word. In one embodiment, the timer that is operated at block 304 is short, and in other embodiments it is long. For example, a delayed memory recognition trial can use a timer value of about 10 minutes or 20 minutes so that the process of blocks 306A to 318 is completed later after the mobile computing device 102 is presented with one or more other intervening tasks.

In one embodiment, the outcome values determined at block 318 are the number of words correctly recognized across the four learning trials and the delayed trial. The timestamps that are collected in the process of FIG. 3 permit the system to determine verbal processing speed metrics for the mobile computing device 102 and thus for the user. Further, the time values obtained from the process of FIG. 3 can be compared with the results of other tests or trials, as described in other sections herein, to report whether the mobile computing device 102 has responded quicker to verbal tests or trials, or spatial tests or trials. As an example, the test app 104 may be programmed to calculate a response time under a first condition minus a response time under a second condition or for a second word, over the sum of the presentations; calculations of this type may reveal the verbal processing rate of the subject rather than just whether or not the subject is capable of remembering words.

In an embodiment, test app 104 may be programmed to receive real-time updates to the word list, in which words are selected based upon prior responses.

In an embodiment, the time interval between block 308 and block 312 may indicate that the user of the mobile computing device is responding relatively slowly, or "staring" at a particular word. In one embodiment, the test app 104 is programmed to monitor the time interval at block 308-310-312 and to replace the word displayed as part of block 306A if the time interval exceeds a particular stored threshold time value.

FIG. 4A, FIG. 4B illustrate example computer screen displays that may be displayed as part of a GO NO GO test. In an embodiment, the GO NO GO test comprises programmed instructions that implement FIG. 2 in which the instruction screen of FIG. 4A is presented at block 204 of FIG. 2, and the prompt of FIG. 4B is displayed at block 206 of FIG. 2. In the GO NO GO test, impulse time and reaction time are measured by presenting the mobile computing device 102 with randomly selected displays of objects having a particular color from among two different colors, such as red and green. The mobile computing device is prompted to tap on red, for example, and not to tap on green. When alternating red and green objects are presented randomly and rapidly in time, the test measures impulse control because an improper tap on a particular color indicates the inability to resist the impulse to tap on that color. When timestamps are integrated and stored, as in FIG. 2, for example by capturing a time stamp of the time of presenting the prompt and the time at which an object is tapped, then the same test also can be used as a measure of processing speed. In such an embodiment, the GO NO GO test as programmed herein can be used to measure how fast the mobile computing device 102 responds to the stimuli and also whether the mobile computing device recognizes the correct stimuli and react to it.

Figure 5B:
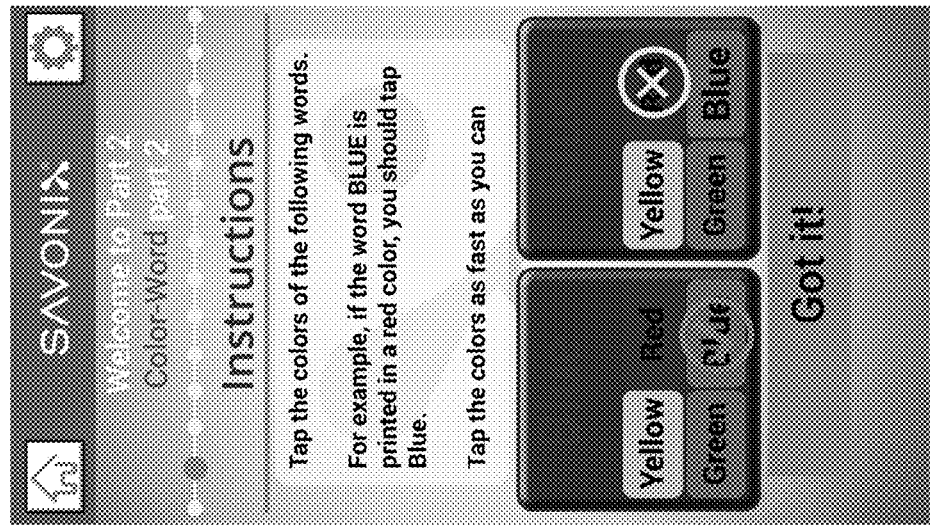
FIG. 5A, FIG. 5B, FIG. 5C illustrate example computer screen displays that may be displayed as part of a COLOR WORD RECOGNITION or VERBAL INTERFERENCE test.
Figure 5A:
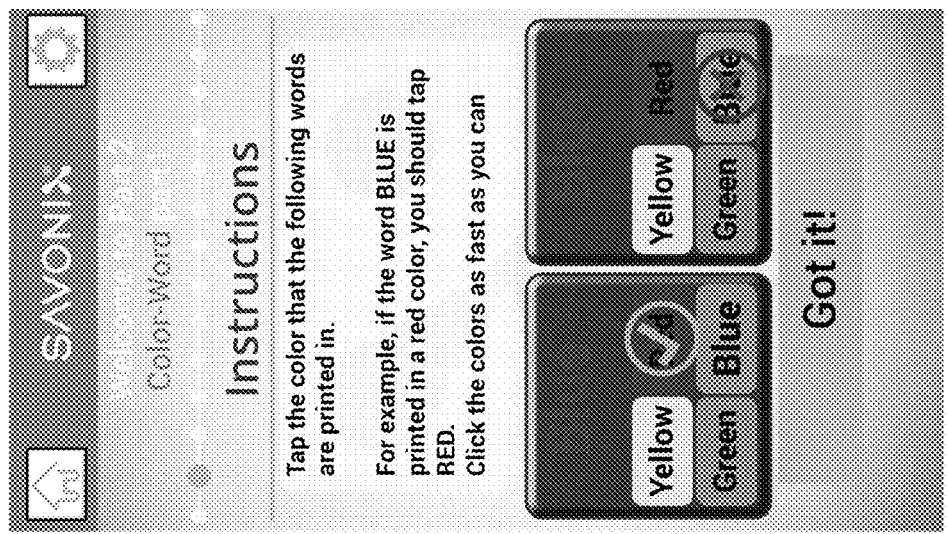
Figure 5C:
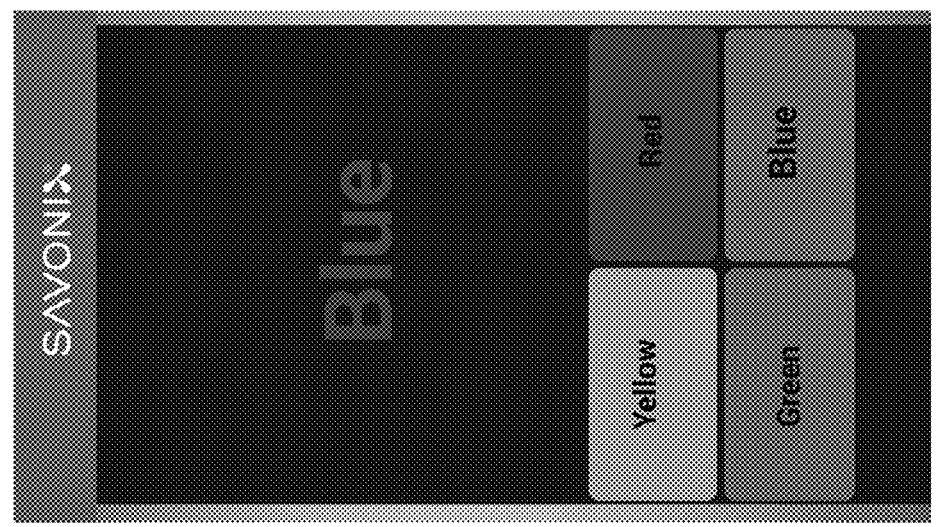

FIG. 5A, FIG. 5B, FIG. 5C illustrate example computer screen displays that may be displayed as part of a COLOR WORD RECOGNITION or VERBAL INTERFERENCE test. In this test, as shown in a first instruction screen of FIG. 5A, the test app 104 is programmed to present, for example, a succession of words using colored type font, and in which the color of the type font does not match the meaning of the word. For example, the word RED may be displayed in a green type font, or the word BLUE is displayed using letters that are colored yellow, as seen in FIG. 5C. The test app 104 is programmed to enforce a first condition to override the language instinct and respond to color, or to override the color instinct and respond to language. For example, in one trial, the mobile computing device 102 displays a prompt page that instructs the user to tap one colored tile, from among a plurality of colored tiles that are shown on the screen, that matches type font or lettering that is the same color. For example, the screen may display colored tiles that are blue, red, yellow and green. In the trial the test app 104 may be programmed to display words that are in those colors, but conflict in meaning with those colors. If the word RED is displayed in blue lettering, then, the user should tap the blue colored tile.

In another trial, in an embodiment, this programming may be altered so that the mobile computing device 102 is instructed to provide input matching the meaning of the word, ignoring the color. In that type of trial, if the word RED is displayed in blue lettering, then correct input would be a tap of the red tile. An example instruction screen appears as FIG. 5B.

In either embodiment, the process of FIG. 2 is used to record time stamps at the time when a test word appears on the screen (for example, RED in blue lettering) and the time at which input is received from the mobile computing device 102 representing a tap on a colored tile. In addition, the test app 104 and/or test instructions 124 are programmed to determine and record whether a response is correct or incorrect. In such an embodiment, test app 104 may be programmed to calculate individual response times to each word based on the time stamps. Additionally, in some embodiments, the total time to complete a trial may be determined and stored. The test app 104 or the test instructions of the server computer may be programmed to correlate the recorded response times to particular colors. In such an embodiment, the server computer can generate report data indicating any difference in individual response items with respect to either of the conditions of the trials. For example, for the word Red, does the first condition (respond to the color) or the second condition (respond to the word name) cause a different response time for a particular mobile computing device 102. This data, in turn, reveals the time that the user of the mobile computing device 102 needs to achieve focus on a task in the presence of a mild distractor (for example, a color) as opposed to a strong distractor (for example, a word), and these response times and focus times can be reported for any trial or test. Only the computer implementation described herein permits the accurate recordation of both results and time for responses.

Figure 6:
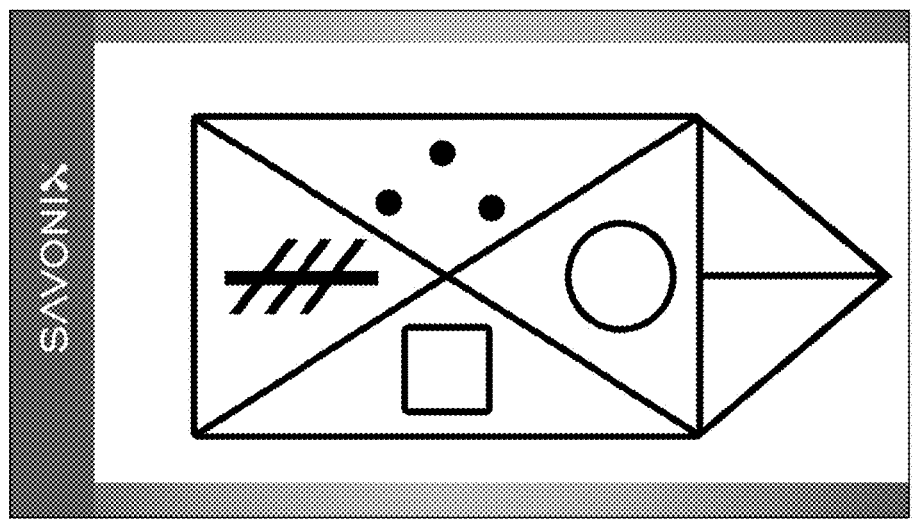
FIG. 6 illustrates an example screen display that may be generated and provided as part of a COMPLEX FIGURE task or test.

FIG. 6 illustrates an example screen display that may be generated and provided as part of a COMPLEX FIGURE task or test. In an embodiment, the test app 104 and/or the test instructions 124 are programmed to display a specified image on the screen of the mobile computing device 102 and continue the display for a specified period of time, for example, 30 seconds. Typically the image comprises a plurality of simple shapes, icons or lines that are position spatially in a particular way. The mobile computing device 102 next is prompted to manipulate the GUI using touch to recreate the image using a grid by drawing or placing shapes or lines. In an embodiment, the process of FIG. 2 is implemented to cause recording a first time stamp when the prompt first appears, and to record successive time stamps in response to each different movement, gesture, tap or touch of the screen of the mobile computing device 102 as the recreation task proceeds. Movements may indicate, for example, dragging or dropping shapes, drawing lines, connecting lines, and other geometric operations. In an embodiment, the test app 104 and/or the test instructions 124 are programmed to analyze and report based on the individual timestamp values whether the user is better at complex icon movement or line drawing recreation, which in turn may suggest the user's mental processing speed for visual spatial elements. As an example, the test app 104 and/or the test instructions 124 are programmed to determine a difference in the time that is taken to place the lines in a diagram as opposed to placing shapes, icons or characters; in this embodiment, each time stamp value may be recorded in memory or other storage in association with a tag indicating whether the time stamp occurred based upon a movement of a shape, icon, character or line. Thus, embodiments may be programmed to measure and report action and response times or time differences separately for different kinds of graphical movement.

Additionally or alternatively, the test app 104 and/or the test instructions 124 may be programmed to repeat a test or trial of the foregoing type in a delayed condition. For example, the test app 104 and/or the test instructions 124 may be programmed to display the specified image on the screen of the mobile computing device 102 and continue the display for a specified period of time, for example, 30 seconds; then present a completely different test or trial; and after a specified time period, for example, 10 minutes, to prompt the mobile computing device 102 next to manipulate the GUI using touch to recreate the image using a grid by drawing or placing shapes or lines.

The foregoing description is for a spatial thinking test that is computer-implemented in a particular way. In another embodiment, the time difference values or response measurements that are determined and/or stored by the test app 104 and/or the test instructions 124 based on the foregoing spatial thinking test may be compared, using other instructions in the test app 104 and/or the test instructions 124, to verbal processing speed values for the same mobile computing device that have been recorded or determined as part of one of the verbal measurement tests that are described in other sections herein.

Figure 7:
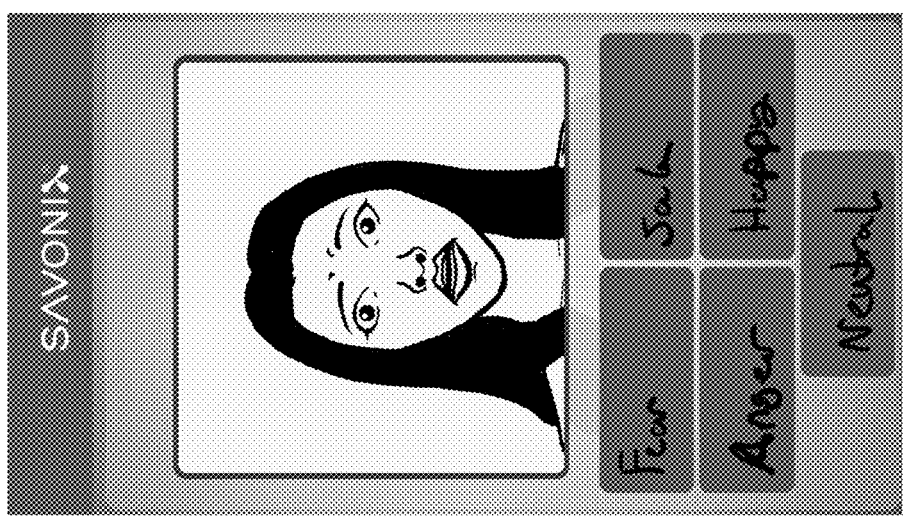
FIG. 7 illustrates an example computer screen display that may be displayed as part of an EMOTION RECOGNITION test.

FIG. 7 illustrates an example computer screen display that may be displayed as part of an EMOTION RECOGNITION test. In an embodiment, the test app 104 and/or the test instructions 124 may be programmed to cause displaying successive images of different human faces on the screen of the mobile computing device 102. Each face image is presented with a plurality of words that state emotions and the test app 104 and/or the test instructions 124 may be programmed to record time stamps in response to the initial presentation of a face image, and in response to detecting a selection response at the mobile computing device 102 indicating a selection of a particular one of the words that corresponds to an expression in the face image. In an embodiment, the test app 104 and/or the test instructions 124 may be programmed to determine the number of correct responses in a set period, and also to determine emotional processing time of the mobile computing device 102 by determining how rapidly the mobile computing device is correctly recognizing positive, neutral or negative emotions based on user selection input, and by determining whether response times the same for the plurality of different emotional cues. In an embodiment, the test app 104 and/or the test instructions 124 may be programmed to determine and/or report response times for multiple different individual emotions that are all categorized as negative, and/or response times for multiple different individual emotions that are all categorized as positive. Such embodiments may help the server computer identify and report an individual emotion that is driving particular decision time values.

Figure 8:
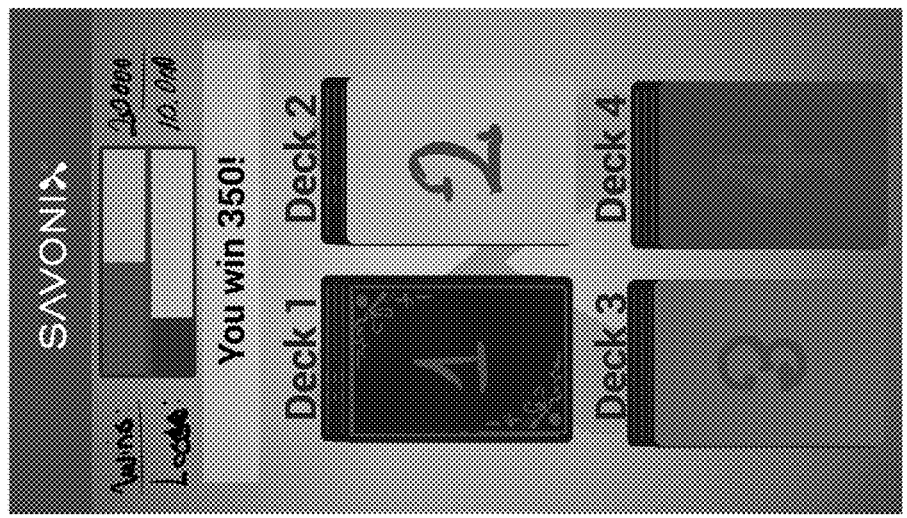
FIG. 8 illustrates an example computer screen display that may be displayed as part of a GAMBLING test.

FIG. 8 illustrates an example computer screen display that may be displayed as part of a GAMBLING test. In one embodiment, the test app 104 and/or the test instructions 124 may be programmed to present images of virtual decks of cards on the screen, or other illustrations that are associated with relative risk differences. The test app 104 and/or the test instructions 124 also are programmed to operate a game environment in which each time the user provides input to the mobile computing device 102 indicating selection of a card, the device is awarded virtual currency which is displayed on the screen; however, at random intervals, selection of a card results in the mobile computing device losing an amount of virtual currency. The goal of the game is to win as much money as possible. Every card drawn will earn the participant a reward. Occasionally, a card will also have a penalty. The decks differ from each other in the number of trials over which the losses are distributed. Thus, some decks are "bad decks", and other decks are "good decks", and because some will lead to losses over the long run, and others will lead to gains.

The process of FIG. 2 is implemented in which time stamps are recorded at the time that a particular card of a desk is first presented and when the mobile computing device 102 detects a response. In this embodiment, the test app 104 and/or the test instructions 124 may be programmed to determine differences in the time stamps to measure decision-making speed in the face of a risk or loss aversion stimulus. In past approaches, decision time has not been measurable in this test. In an embodiment, the test also measures impulse control, because the mobile computing device 102 detects a response when the user has decided not to restrict themselves from giving a response. In an embodiment, the test app 104 and/or the test instructions 124 may be programmed to compare time values resulting from this decision-making to those from the other tests, to provide a more broad view of how times for decision change in the face of different conditions.

Figure 9:
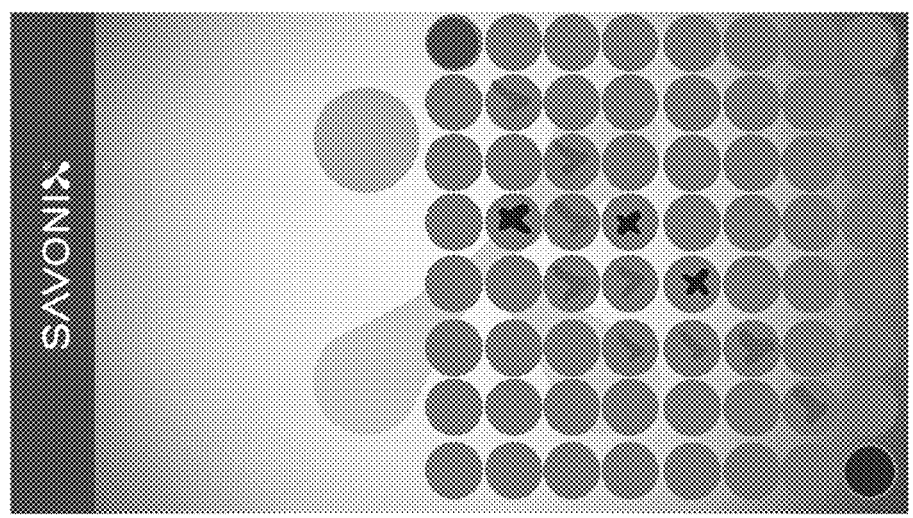
FIG. 9 illustrates an example screen display that may be displayed as part of a MAZE task.

FIG. 9 illustrates an example screen display that may be displayed as part of a MAZE task. In an embodiment, the test app 104 and/or the test instructions 124 are programmed to cause displaying a maze on the screen of the mobile computing device 102, and then monitor responses of the mobile computing device that indicate path discovery through the maze, step by step. Thus, in an embodiment, the test app 104 and/or the test instructions 124 are programmed to record a first time stamp value when the maze is initially presented and also to record successive time values as the mobile computing device 102 provides response data indicating the selection of a point within the maze. Using this approach, the test app 104 and/or the test instructions 124 are programmed to measure real-time learning, as each wrong selection requires the mobile computing device 102 to provide input indicating a backtrack and trying another path. In an embodiment, the test app 104 and/or the test instructions 124 are programmed to provide a second, similar trial in which the identical hidden path is represented in stored digital data, but the mobile computing device is tested on speed of remembering and problem solving. In this approach, the test app 104 and/or the test instructions 124 are programmed to record timestamps stepwise as movement through the maze occurs, so that the test app 104 and/or the test instructions 124 can reveal step to step timing as success occurs or as errors occur. Long differences in response times may indicate instances of confusion or stalling within the maze. The test also is effective indicating the capacity to learn and recall recent data, such as the position of erroneous paths in the maze; in an embodiment, the test app 104 and/or the test instructions 124 are programmed to determine one or more patterns in processing that are revealed by the timing of responses during maze traversal. For example, the programming may indicate a number of steps during maze traversal that a particular mobile computing device 102 completes rapidly, followed by a section that is traversed slowly. Output values from this form of testing and analysis may indicate, for example, the maximum set of data that a particular user is capable of processing, which may be relevant to education, coaching and adult learning by indicating the size of appropriate lessons.

The foregoing description is for a spatial thinking test that is computer-implemented in a particular way. In another embodiment, the time difference values or response measurements that are determined and/or stored by the test app 104 and/or the test instructions 124 based on the foregoing spatial thinking test may be compared, using other instructions in the test app 104 and/or the test instructions 124, to verbal processing speed values for the same mobile computing device that have been recorded or determined as part of one of the verbal measurement tests that are described in other sections herein.

Figure 10:
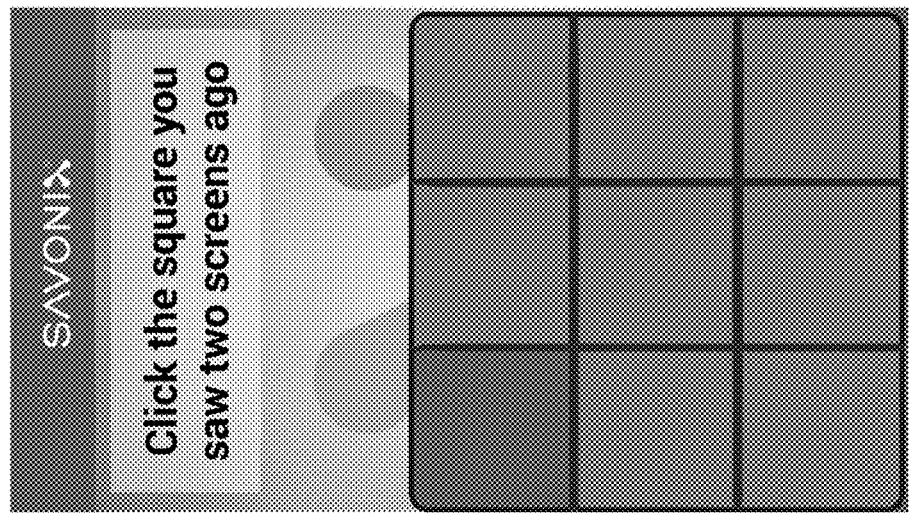
FIG. 10 illustrates an example computer screen display that may be displayed as part of an N-BACK TASK.

FIG. 10 illustrates an example computer screen display that may be displayed as part of an N-BACK TASK. In an embodiment, test app 104 is programmed to present the mobile computing device 102 with a sequence of visual stimuli using the display screen, and the task consists of indicating when the current stimulus matches a stimulus that was presented n instances earlier in the sequence. For example, in one trial, test app 104 may be programmed with a value of n=2, and to display a sequence of graphical objects comprising a star, a diamond, a square and a circle, followed by the square again in conjunction with a YES/NO prompt. Because the square was presented two instances earlier in the sequence of (star, diamond, square, circle), the correct answer is YES. The load factor n can be adjusted to make the task more or less difficult, for example 1<=n<=5 in various trials. In an embodiment, the process of FIG. 2 is used, and timestamps are recorded only when the prompt object is displayed, such as the square in the preceding example, and when a response is received to that response. In such an embodiment, report data may measure or indicate both response time, per individual prompt object or as a mean or series of values for an entire trial, and the number of correct and incorrect answers.

Thus, in an embodiment, test app 104 implements the N-BACK TASK as a test of working memory. The test investigates not just whether the mobile computing device 102 indicates that the user remembered that they saw an object before, but how much data the user can hold in their mind, as measured by the computer, while maintaining accuracy; speed of the user also is measured and can indicate whether the user has good mental processing speed. Embodiments as described herein also can be used for the server computer or test app 104 to calculate the verbal processing speed of the mobile computing device 102 as compared to the spatial processing speed indicated by the data. In these embodiments, the programming of test app 104 as shown in FIG. 2 and described above permits measuring and reporting this data to the millisecond.

Figure 11B:
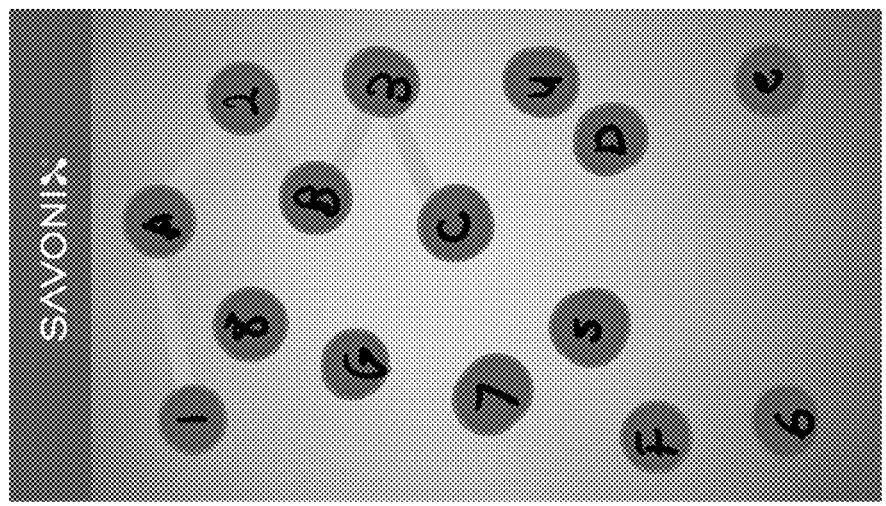
FIG. 11A, FIG. 11B illustrate example screen display that may be displayed as part of a TRAIL MAKING (CONNECT THE DOTS) test.
Figure 11A:
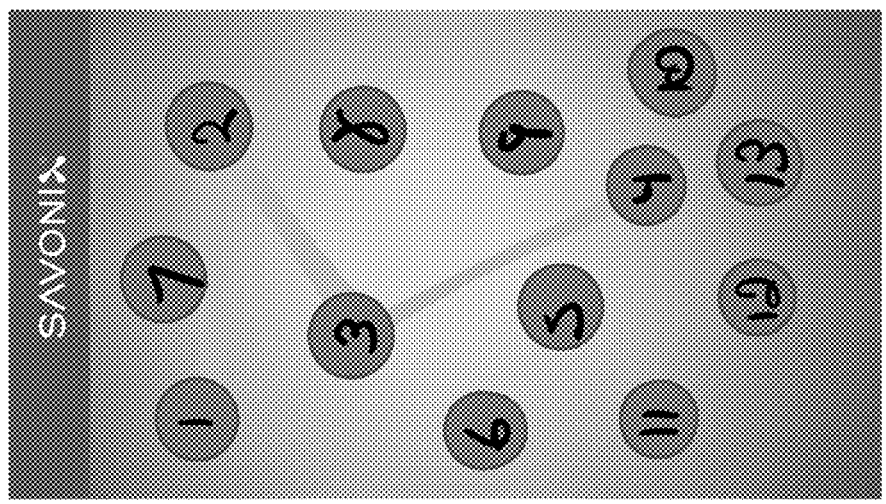

FIG. 11A, FIG. 11B illustrate example screen display that may be displayed as part of a TRAIL MAKING (CONNECT THE DOTS) test. In an embodiment, the test app 104 and/or the test instructions 124 may be programmed to display a matrix of points or dots, receive input from the mobile computing device 102 indicating selections of successive different points or dots, and provide responses indicating a correct connection or an error. In this approach, the process of FIG. 2 is implemented by recording a time stamp value when the matrix is first presented, and as each input selection occurs. Each administration of the test is based upon stored digital data representing a correct path or trail that traverses a sequences of the points or dots, but which is initially hidden from view. As responses are received, the test app 104 and/or the test instructions 124 may be programmed to display either a line segment indicating a correct traversal to the particular point or dot, or an error notification. Thus, when the test app 104 and/or the test instructions 124 receives input from the mobile computing device 102 indicating a correct sequence of numbers, then a path or trail is drawn on the screen whereas the selection of an incorrect point along the hidden path or trail produces a warning notification. Recording timestamp values as input is received from the mobile computing device can provide a measure of executive function, focused attention measure, and/or flexible thinking. In an embodiment, the test app 104 and/or the test instructions 124 are programmed to record the time that is incurred to traverse the path or trail stepwise; thus a plurality of step time values are detected and recorded as each step on the path or trail is traversed. These values may permit the test app 104 and/or the test instructions 124 to determine whether the mobile computing device 102 provides responses faster as the path continues, or slower. Thus, the recorded time values may be used by the test app 104 and/or the test instructions 124 to determine whether a complex task causes reduction in speed over time.

The foregoing description is for a spatial thinking test that is computer-implemented in a particular way. In another embodiment, the time difference values or response measurements that are determined and/or stored by the test app 104 and/or the test instructions 124 based on the foregoing spatial thinking test may be compared, using other instructions in the test app 104 and/or the test instructions 124, to verbal processing speed values for the same mobile computing device that have been recorded or determined as part of one of the verbal measurement tests that are described in other sections herein.

In an embodiment, the process of FIG. 2 may be programmed to implement an EMOTIONAL STROOP test. In an embodiment, test app 104 is programmed to cause displaying, for example, color blocks in a square of four blocks, each of which contains a word that is emotionally loaded, and to prompt the mobile computing device to tap the corresponding color. The test challenges the user to ignore the content of the word and thus imposes an emotional distraction that can affect performance. In an embodiment, the process of FIG. 2 is performed and time stamp values are recorded when a particular set of blocks with particular words is displayed, and when the mobile computing device 102 detects a response. In this approach, the test app 104 and/or the test instructions 124 may be programmed to determine time difference values that indicate the amount of time needed to override cues provided in language for negative, neutral and positive words. Further, the test app 104 and/or the test instructions 124 may be programmed to determine response time by color and to provide reports or graphical displays indicating the response times by color for a particular mobile computing device 102 or user. Because timing is critical to the accuracy of this test, a computer-timed test is more accurate than has been possible in any past approach.

In an embodiment, the process of FIG. 2 may be programmed to implement a DIGIT SPAN test. In an embodiment, the test app 104 and/or the test instructions 124 are programmed to implement a test of working memory in which the screen of the mobile computing device 102 is driven to display a plurality of successive digits and then to await user input specifying a set of the digits that were previously displayed. For example, the mobile computing device 102 may be prompted to enter response input indicating the last three digits that were displayed. In an embodiment, the test app 104 and/or the test instructions 124 are programmed to capture the time to enter digits and the elapsed time to start and complete the trial. Further, the test app 104 and/or the test instructions 124 may be programmed to determine, on the basis of the recorded time stamp values, whether the mobile computing device 102 speeds up or slows down as digits are entered. The process of FIG. 2 may be implemented in a manner in which each tap of the screen of the mobile computing device 102 is recorded as a response with an associated time stamp, and the total time to perform the test is computed based on an ending time stamp. In these embodiments, the test app 104 and/or the test instructions 124 are programmed to measure working memory processing speed, not just accuracy. Thus, the test app 104 and/or the test instructions 124 effectively measure, as the user is asked to hold more information, how does processing time change.

In an embodiment, the process of FIG. 2 may be programmed to implement a VERBAL FLUENCY test. In an embodiment, the test app 104 and/or the test instructions 124 are programmed to cause displaying a letter of the alphabet on the screen of the mobile computing device, alone or in conjunction with a text prompt that instructs the user to recite as many words as the user knows that begin with that letter and that are not proper nouns. In an embodiment, the test app 104 and/or the test instructions 124 are programmed to record a time stamp at the moment that the letter prompt is presented, to record utterances of words using a microphone of the mobile computing device 102 and a set of speaker-independent voice recognition instructions, and the amount of time that elapses between utterances of words. In an embodiment, the test app 104 and/or the test instructions 124 are programmed to transform a spoken utterance into a recognized word in a particular language, and to determine whether the particular utterance corresponds to a word in a digitally stored dictionary for that language. In an embodiment, the test app 104 and/or the test instructions 124 are programmed to determine whether successive words have a common root, and if so, to record a weighted value corresponding to speaking that word. For example, distinct words that correctly begin with the specified letter may result in storing a credit value of "1.0" and a successive word that uses the same root as a previous word may result in storing a credit value of "0.5". For example, if the specified letter is "B" and the mobile computing device 102 records utterances of "BEGIN," "BEGINNER," "BEGINNING," then the test app 104 and/or the test instructions 124 may be programmed to store credit values of 1.0, 0.5, and 0.5.

Additionally or alternatively, in an embodiment, the test app 104 and/or the test instructions 124 are programmed to determine an entropy value indicating the magnitude of difference between two successive words and to use the entropy value to determine or scale the credit value.

Additionally or alternatively, in an embodiment, the test app 104 and/or the test instructions 124 are programmed to determine a language entropy value indicating the magnitude of difference between the languages of two successive words and to use the entropy value to determine or scale the credit value. For example, an English word followed by a French word and a Croatian word may result in increased credit values for the French and Croatian words as the use of multiple languages is associated with greater intelligence.

Unlike past approaches, the implementation of the verbal fluency test as described above is capable of recording word utterances with timestamps at a pace far faster than a human observer would be capable of.

Embodiments of all the computer-implemented tests described above also eliminate bias, error or distraction introduced by the human investigator. Timestamp values that are recorded can be correlated to time of day, day of the week.

In some embodiments, presentation instructions 126 implement a web-based dashboard, in conjunction with HTTP server instructions 128, having selectable options to cause displaying individual and group results in detail, including for example individual response times per test per response, and percentile scores on all the tests. In some embodiments, analysis instructions 116 may be programmed to generate and cause displaying a BRAIN PROFILE TYPE, for a particular user of the mobile computing device 102, or for a group of devices or users that are defined by an administrative user. In an embodiment, presentation instructions 126 may be programmed to receive input specifying to view and manage records of all users of the system, individually or by groupings. Example groupings may include all users with a specified diagnosis in a clinical setting, or all users who are applicants for a specified job. In an embodiment, presentation instructions 126 may be programmed to receive input specifying selections of graphical views of the groupings and to generate spreadsheets and reports.

In some embodiments, the test app 104 and/or the test instructions 124 are programmed to prompt the mobile computing device 102 to provide demographic data values relating to the user of the mobile computing device, to permit generating normative results or percentile rankings based on the demographic data values.

In an embodiment, the analysis instructions 116 may be programmed to execute one or more algorithms that assess response data values including values indicating correct or incorrect responses, and time stamp values, to generate feedback to an administrative user such as a clinical psychologist, human resources representative, or other individual, computer or system. In some embodiments, analysis may comprise obtaining a possible range of scores for the tests, determining a normative distribution of possible scores, determining actual scores of users, placing the actual scores in positions within the normative score, and based upon the positions, selecting from one or more stored particular statements to result in generating a report that contains statements about the cognitive and emotional intelligence and function of the particular user.

Figure 12:
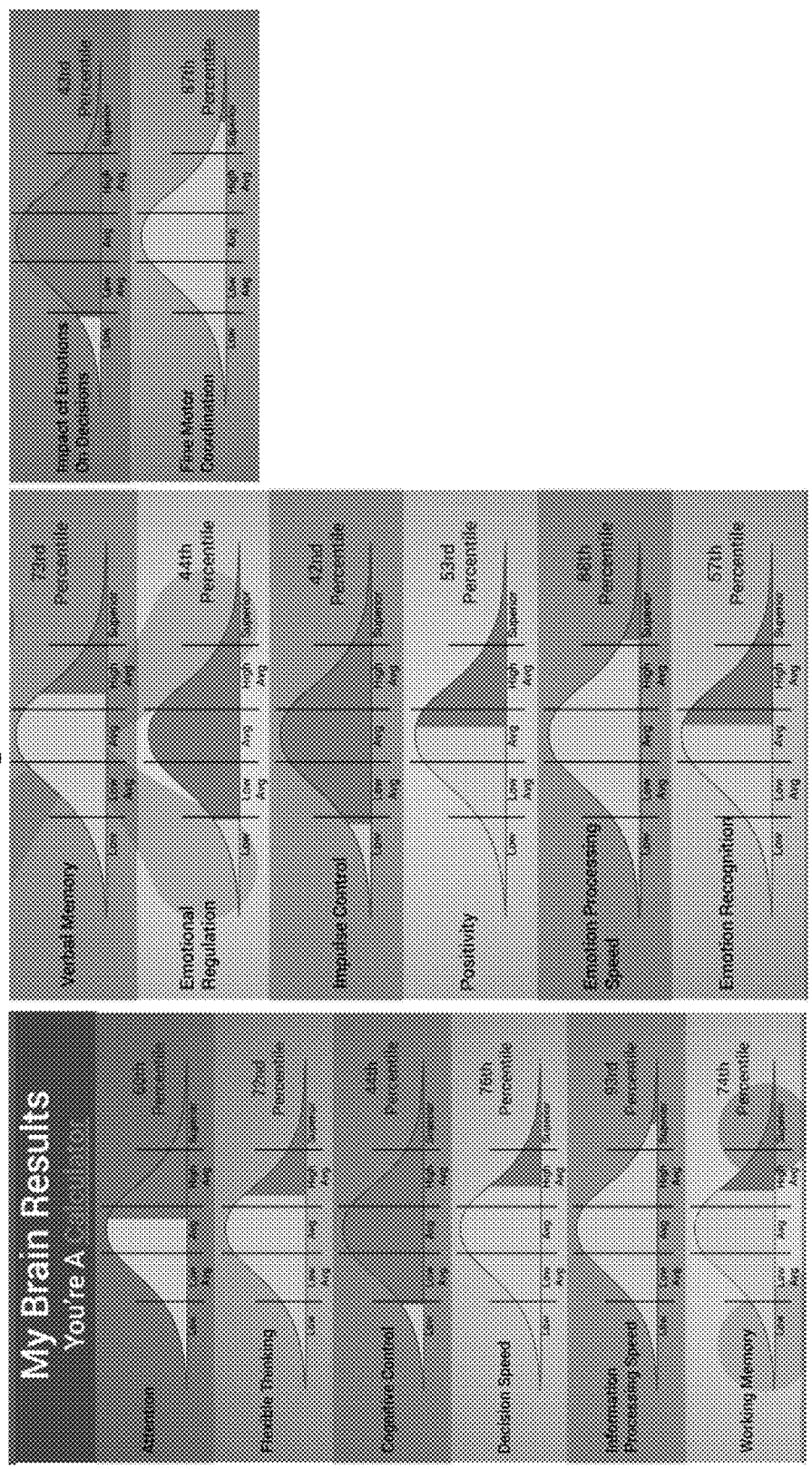
FIG. 12 illustrates an example of a reporting screen for BRAIN PROFILE TYPE in which an overall brain profile type ("Calculator") is indicated together with a plurality of result graphs.

FIG. 12 illustrates an example of a reporting screen for BRAIN PROFILE TYPE in which an overall brain profile type ("Calculator") is indicated together with a plurality of result graphs. Each of the result graphs is labeled with a domain (for example, "Verbal Memory" and indicates the user's position in a normal distribution of previously recorded or known results for tests that are relevant to that domain or that result in scoring for that domain. The number of result graphs, their labels, and the specific data presented in FIG. 12 are provided solely to illustrate a clear example and other embodiments may vary.

Alternatively, Z-score calculation can be used as an alternative to chunking result data over a normal distribution.

The foregoing example has described an embodiment in which one or more of the individual tests may be combined in a battery of tests to assess multiple domains of cognitive and emotional intelligence and function. In one embodiment, ten tests selected from those above are administered using the test app 104, and the tests are presented serially to the mobile computing device. Not all embodiments of test app 104 and/or test instructions 124 need to implement all the tests that have been described herein.

It will be noted that some of the tests report on multiple different cognitive domains. The aggregate score resulting from two or more tests can be used to provide a more accurate result or report with respect to a particular single cognitive domain. For example, the color word test described herein may be used for blending color and language to measure distraction, but also can be used also to measure aspects of attention. By recording the number of responses within the allotted time, as well as correct responses, and response time, embodiments permit developing new forms of assessment, reporting and outcome data based on the response time values. Thus, embodiments may be programmed, as part of post-processing at step 222 for example, to generate and display processing speed values or scores for one or more individual areas of function, such as visual, spatial or verbal, and based on individual processing speed values or scores for those domains, the system may be programmed to generate a total processing speed score or global processing speed score by computing an average or arithmetic mean of all the individual processing speed scores. The total processing speed score or global processing speed score may be generated, output and displayed at step 222, for example.

Figure 13:
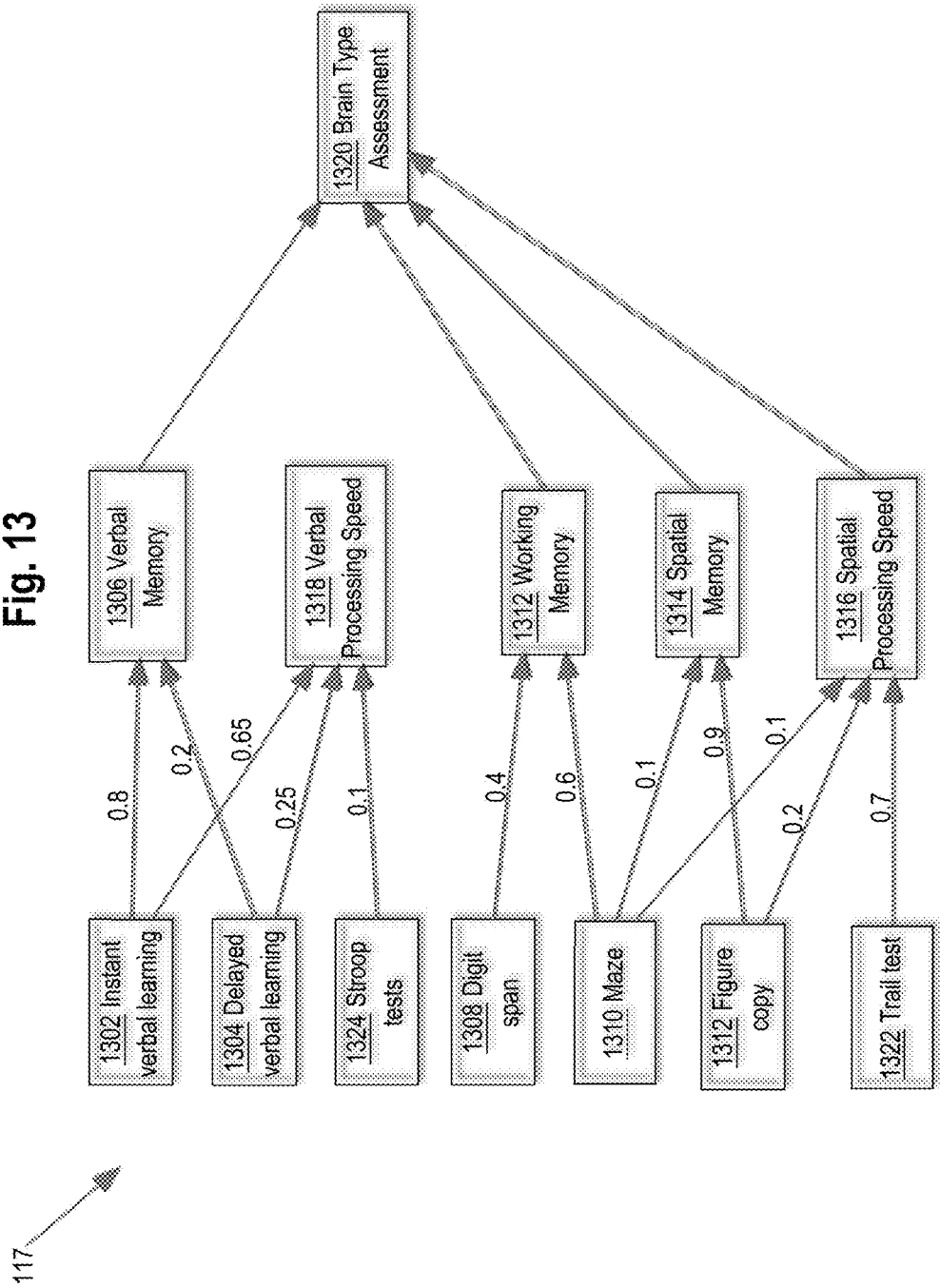
FIG. 13 illustrates an example of cross-correlation of tests to cognitive domain results that may be implemented using analysis instructions or other logic.

Computation using an average, or arithmetic mean, is not required in all embodiments. FIG. 13 illustrates an example of cross-correlation of tests to cognitive domain results that may be implemented using analysis instructions or other logic. As seen in FIG. 13, in one embodiment, test correlation instructions 117 may be programmed to obtain scores or results of a plurality of particular tests, applying different weighting factors to the individual scores, and apply the resulting weighted sum as a score for a particular cognitive domain. In general, as provided in FIG. 13, test correlation instructions 117 are programmed to apply scores from two or more tasks, indicated with reference numerals for tasks 1302, 1304, 1324, 1308, 1310, 1312, 1322, to scores in one of more of the cognitive domains 1306, 1318, 1312, 1314, 1316, and all the cognitive domain scores contribute to a brain type assessment 1320. Clinicians will recognize that FIG. 13 is necessarily simplified for the purpose of presenting a clear example, and other embodiments may implement cross-correlation techniques that are more complex.

As one example, in the approach of FIG. 13, a score of a user from an instant verbal learning task 1302 is weighted to have a contribution of 80% to assessment of the verbal memory domain as indicated by the arrow labeled "0.8" extending to verbal memory domain 1306. The delayed verbal learning task 1304 has 20% weight. Both the instant verbal learning task 1302 and delayed verbal learning task 1304 also contribute to the verbal processing speed domain 1318, but with different weight values of 65% and 25% respectively; scores from one or more stroop tests 1324 contribute 10% to the verbal processing speed domain. Each of the domains 1306, 1318, 1312, 1314, 1316 is associated with inputs that sum to 100%.

In some embodiments, each of the score values obtained from tasks 1302, 1304, 1324, 1308, 1310, 1312, 1322, after application of the weight value shown adjacent to the arrows, may result in a position within a normal distribution that may be shown in a graph as seen in FIG. 12.

Generating a brain type assessment 1320 may include generating and outputting a global or total processing speed value or score based on blending the individual score values based upon weight values as seen in FIG. 13. It will be noted that tasks 1302, 1304, 1324, 1308, 1310, 1312, 1322 provide individual scores in one of more of the discrete cognitive domains 1306, 1318, 1312, 1314, 1316. The aggregate score resulting from two or more tests or tasks can be used to provide a more accurate result or report with respect to a particular single cognitive domain. For example, the color word test described herein may be used for blending color and language to measure distraction, but also can be used also to measure aspects of attention. By recording the number of responses within the allotted time, as well as correct responses, and response time, embodiments permit developing new forms of assessment, reporting and outcome data based on the response time values. Thus, embodiments may be programmed, as part of a brain type assessment 1320 for example, to generate and display processing speed values or scores for one or more individual areas of function, such as visual, spatial or verbal, and based on individual processing speed values or scores for those domains, the system may be programmed to generate a total processing speed score or global processing speed score by computing an average or arithmetic mean of all the individual processing speed scores. The total processing speed score or global processing speed score may be generated, output and displayed as a brain type assessment 1320, for example.

Use of a touch screen with a mobile computing device permits capturing response time to the millisecond and permits the analysis instructions 116, for example, to determine when the subject has developed an analysis and response strategy. In this manner, results of all tests defined herein can be correlated to the processing speed domain; only the computer implementations described herein permit capturing accurate, real-time responses in the dataset and using actual response time values, per test, per user, and per response, to assess processing speed. In turn, the response time data permits programming the analysis instructions 116 to calculate the information processing speed of the brain of a particular user, and determining the real time difference between processing data with or without distractors. Further, assessment of differential response time values using analysis instructions 116 permits the computer to determine a point at which a significant change in response time occurs in successive responses of a test or trial, which may indicate mastery of the test or development of a test-taking strategy. In sharp contrast, in past approaches, the precise amount of time taken to respond to individual stimuli has not possible, and permits all the tests defined herein to assess processing speed, as well as permits cross-domain correlation of processing speed to other aspects of cognition.

A distinct benefit of embodiments is that shortened, minutes-long tests may be used with the same clinical value as hours-long tests that have been administered in past, paper-based approaches. For example, in paper-based administrations of an N-back test, eight to ten trials are typically done; in embodiments here, two trials of the computer-implemented N-back test described above has been found to be representative of clinical results.

3.2 Second Functional Example—"Neuronet" System

In an embodiment, all tests that comprise the battery of an implementation of this disclosure, termed NeuroNet, are delivered via a mobile device. Scoring and analysis, including a full report from the tests, are built into the platform analytics. NeuroNet is cost effective, short (30-40 minutes) and does not require a clinician for administration, scoring, or report generation. Individual user results are readable in full on the mobile device. The Enterprise (EPP) product also offers a desktop or laptop interface that enables viewing of individual and group results across a NeuroNet system, such as in a corporate or clinical setting.

This invention is an improvement on what currently exists. No other application exists with wholly computerized, mobile testing, scoring and report generation in neurocognitive screening or assessment. Existing tools still rely on a clinician for administration, scoring, and report generation. Pen and paper versions are subject to human error particularly when recording response time scores and nothing is available via a mobile platform with 100% computerized administration, scoring, and report generation.

NeuroNet provides 100% mobile 100% computerized administration, testing, scoring, and interpretation of results of a standardized neuro-cognitive battery of valid reliable tests of cognitive and emotional intelligence domains. It provides results at the individual user level as well as at the enterprise level, allowing an employer or clinician a view of results across all users on their license.

Also, it can produce: This invention produces a brain type report and cognitive domains results for the tests (steps) administered in the assessment. It also produces enterprise-level database tracking reports and presentations of individual and group level results.

An embodiment may include logic to execute or present:

1. Intro to NeuroNet: A short demographics questionnaire to establish factors such as identity, gender, age and education level to provide normative/percentile scores in the results section. A brief screen/page is presented that demonstrates how to take the NeuroNet assessment and gives the user instructions to begin the assessment. The user is informed that audio (indicated in the application by small ear icons) instructions are available for each test (step) in NeuroNet by clicking on the ear icon at any time.

2. Complex Figure Copy Task: Users are required to view a complex image and then reproduce it from memory immediately and in a delayed condition (10 minutes later) using the touchscreen on the smart device.

3. Gambling Task: Users are presented with 4 virtual decks of cards on the screen. They are told that each time they choose a card they will win some game money. Every so often, however, choosing a card causes them to lose some money. The goal of the game is to win as much money as possible. Every card drawn will earn the participant a reward. Occasionally, a card will also have a penalty. The decks differ from each other in the number of trials over which the losses are distributed. Thus, some decks are "bad decks", and other decks are "good decks", and because some will lead to losses over the long run, and others will lead to gains.

4. Verbal Memory Recognition—Verbal List-Learning Task: The users are presented with 12 words, which they are asked to memorize and recognize later from memory. The list contains 12 concrete words from the English language. Words are closely matched on concreteness, number of letters, and frequency. The list is presented 4 times. After each trial, the user is required to recognize as many words as possible by choosing between 20 sets of word pairs on the screen. One is correct and the other a distractor word. A delayed memory recognition trial is completed approximately 10 minutes later after a number of intervening tasks. The outcome variables are the number of words correctly recognized across the four learning trials and the delayed trial.

5. Find-the-Word Task: Users are presented with two words on the touch-screen. One of the two words is a valid word in the English language and the second is a non-word foil. Users are required to identify which of the two words is the real word. Outcomes are measured in response time per trial as well as the number correct and incorrect answers.

6. N-Back Task: Users are presented with a sequence of stimuli, and the task consists of indicating when the current stimulus matches the one from n steps earlier in the sequence. The load factor n can be adjusted to make the task more or less difficult, for example screen immediately prior or 3 prior to the current screen/frame task of recall for the test. The visual n-back test is similar to the classic memory game of "Concentration". However, instead of different items that are in a fixed location on the game board, there is only one item, that appears in different positions on the game board during each turn. N-back works like this; 1-N means that you have to remember the position of the item, ONE turn back, 2-N means that you have to remember the position of the item TWO turns back, and so on. Outcomes are measured in response time and the number correct and incorrect answers.

7. Verbal Interference: This task taps the ability to inhibit automatic and irrelevant responses. The user is presented with colored words, one at a time. Each word is drawn from the following set of words: "red", "yellow", "green" and "blue". Below each word printed in a congruent or incongruent color is a response pad with four color tiles in red, blue, yellow and green. The test has two parts. In part 1, the user is told to tap the color tile that corresponds to the word as fast as possible. For example if the word red is printed in blue the user would tap the red tile for a correct response. In part 2, the user is required to tap the color tile that corresponds to the color the word is printed in on the screen ignoring the text of the word, blue for a correct response from the previous example. Each part lasts for 1 minute. Responses are made on the screen by tapping the appropriate color box on the touch screen. The outcome variable in each part is the number of correct responses. Response times are also measured for each trial.

8. Switching of attention task: The user is presented with a pattern of 14 numbers (1-13) and 12 letters (A-L) on the screen and is required to touch numbers and letters alternatively in ascending sequence (i.e. 1 A 2 B 3 C . . . ). As each number or letter is touched in correct order, a line is drawn automatically to connect it to the preceding number or letter in the sequence. This allows the user to visualize the path touched. This task tests the ability of the user to switch attention between mental tasks; in this case number and letter sequence checking, and thereby alternate between the respective mental sets induced. The outcome variable is time to completion as well as number of correct responses versus incorrect responses.

9. Maze Task: The user is presented with a grid (8×8 matrix) on the device screen. The object of the task is to identify the hidden path through the grid, from the beginning point at the bottom of the grid to the end point at the top. The user is able to navigate around the grid by tapping on parts of the grid or swiping a path through the grid. A total of 24 consecutive correct moves are required to complete the maze. The user is presented with a red "x" if they make an incorrect move, and a green "check mark" if they make a correct move. The task serves to assess how quickly the user learns the route through the maze and their ability to remember that route. Only one maze is presented across trials, and the test ends when the user completes the maze twice without error or after 5 minutes have elapsed. The outcome variable is the total number of correct responses versus errors and it also measures response time overall and for individual moves within the maze navigation.

10. Emotion Identification Task: This is test of emotional recognition. Users are presented with a series of faces with different emotional expressions (i.e. surprise, fear, disgust, happy, neutral). Users tap a button on the touch screen to correctly name the emotion expressed on the face for each trial. The goal is to identify the correct emotional expression presented by the faces. The outcome variable is the total correct versus incorrect answers and the test also measures response time for identifying the emotion on each face presented.

11. Go-No-Go: A green circle is presented frequently (Go) and a red square infrequently (No-Go). The user is required to tap quickly on the circle and resist tapping on the square. This task measures target detection rate, response time, and errors of commission and omission. It is used to assess the capacity for suppressing well-learned, automatic responses. The outcome variable is the number of correct versus incorrect answers, and response times are measured for each frame as well as for the test as a whole.

12. A dashboard provides a main menu page for the user that includes links to pages in the application such as a results page with bell curve ratings for each cognitive domain, a brain type report page, information about each cognitive domain with definitions, information about the science and research behind NeuroNet, an icon connecting the user to brain training games in areas assessed as needing improvement, and to the user's personal profile and account information.

13. A web-based enterprise dashboard is available for EPP customers to view individual and group results in detail, down to response times and percentile scores on all the tests, as well as the "Brain Profile Type" for each user, and even in groups customized by the EPP client. The EPP customers that purchase NeuroNet's suite of complimentary prescriptive training games for cognitive and emotional intelligence can also access the NeuroNet results generated training recommendations. The Dashboard will offer multiple enterprise options such as the ability to view and manage all users on the EPP license individually or by groupings. Example groupings might include diagnosis in a clinical setting, or job applied for, or department in a Human Resources setting. The dashboard will allow for graphical views of the groupings and the ability to push-button generate spreadsheets and reports. Drawings of this dashboard are not included as it is quite extensive.

14. Throughout NeuroNet, countdown screens are used in between the tests (steps) to prepare the user for the beginning of each individual test (step) so they are prepared for it to start.

In an embodiment, together, the elements described above comprise a battery of tests to assess multiple domains of cognitive and emotional intelligence and function. Step 1 establishes demographics for normative results (percentile rankings) and provides information on how to use the NeuroNet app. Each test listed (i.e. go-no-go, maze, etc.) when administered together as part of a grouping of such tests comprises a "battery" that provides end results across multiple domains of cognitive and emotional intelligence and function. Steps 2-11 (the tests) comprise the "battery". Steps 12 and 14 provide the individual and group level scores and report generation for interpretation of the results. Step 14 is used here to describe a between-test feature that enhances the user friendliness of the NeuroNet application.

Embodiments provided automated selection among a set of tests with individual attributes to measure various domains of cognitive and emotional function and the collection of such tests into a "grouping" that is administered together as a "battery" assessment to measure multiple domains of cognition and emotional intelligence and function. NeuroNet automates this process of selecting tests to comprise a Battery using a mobile-based application for the administration, scoring, interpretation, and report generation by using a standard pre-selected battery of tests described above. The demographic data, individual test scores, and timed responses may be used to compute the final percentile scores in domains such as attention, processing speed, and working memory. The tests were specifically selected to work together to provide the maximum cognitive and emotional intelligence and function data in as short a time as possible in an automated format. For instance, the complex figure copy task provides data that is factored into the final scores and report data in the domains of visuospatial abilities, memory, attention, planning, and working memory or executive functions. The mobile device replaces the clinician in this process by providing detailed written and audio instructions for each individual test or step and then the computer also scores and interprets the data individually and in-aggregate to produce an integrated report of all the results from the individual steps or tests in the battery.

There are many more relationships between the various tests and the assessment of the final brain profile types and normative percentile results. For example, the user is asked in Step 1 if the person is colorblind. If the answer is yes, then the platform does not score the color word interference test, as it would not measure real cognition but rather failure due to color blindness. In the report generation, the cognitive domains and brain type reports are the result of complex formulas that look at the relationship between results across all the tests (steps 2-11) in relationship to one another to generate the brain type report and percentile scores for each cognitive domain. For instance, processing speed is a score that is derived from response time measures for frames across multiple individual tests in the NeuroNet Battery.

In an embodiment, NeuroNet is software and is built on a complex database and back end that supports the administration, scoring, interpretation, and reporting of the test results in the battery. The user interface (UI) presents the tasks associated with each step at a particular frame speed and rate determined by research data on normative response times by age for each test (for example it should take 0.267-0.400 seconds to respond to each Go-No-Go frame presented in that test across ages 6 to end of life). The software is written to run the tests on established and published norms for these test, then to score and interpret those results again according to established and published norms.

All of the elements are necessary for the battery to function as a fully mobile, computerized assessment that does not need a clinician for administration, scoring, interpretation and report (brain type) generation.

The tests (steps 2-11) could be administered in a different order, with different UI, different total time per test or different scoring specifications and it would be the same battery and it would be an equivalent product. For example, Go-No-Go could be done with the instructions to press when a word or a color appears instead of the circle and square as in our test (step) and it would be an equivalent product.

Individual tests (steps 2-11) could be substituted with a similar (equivalent) measures and it would be an equivalent or identical product in terms of utility. Examples of such potential test (step) substitutions are: A spoken verbal fluency test instead of find the real word task could be administered or a different figure (image) could be used for the figure copy task and it would be equal.

Any of the tests (steps 2-11) could be given for a different length of time, for example a 45 second or 1 minute trial instead of our thirty second trial for Go-No-Go and it would be equivalent.

Other tasks/tests that are equal to the ones we have chosen to include and which would constitute an equal test replacement for one of the steps are verbal fluency, the emotional stroop task (identifying if the face presented and the word presented are congruent such as a smiling face with the word happy or incongruent such as a smiling face with the word fear), any kind of vocabulary test or word finding or identification test, a matrix or other pattern recognition/completion test, a digits or other stimuli (i.e. images) forward and/or backward recall test, any maze navigation or path finding task/test, any kind of pattern copy task such as arranging shapes or blocks to match a presented image from memory, and any type of card sorting task.

Clinicians might use NeuroNet, in various embodiments, to replace human-performed neuro-cognitive screens for emotional and cognitive domains of intelligence and function in their practice to save time and lower the costs associated with such assessments. Companies might use NeuroNet to screen potential or current employees for specific traits such as impulse control, impact of emotions on decisions, attention to detail, social skills, or overall emotional intelligence. Researchers might use NeuroNet to replace costly clinician administered neuro-cognitive screens in their medical or clinical research. The military might use it to screen soldiers for neuro-cognitive function. Individuals might use it to assess themselves and better understand their brain type and brain function, and to get personalized recommendations for brain training games, which can be implemented separately, and/or in conjunction with the NeuroNet tool. In each of these cases NeuroNet provides a mobile, cost effective, time saving, accurate and valid, reliable solution.

In an embodiment, the system produces a brain type profile report and cognitive results for the tests (steps 2-11) administered in the program. It also produces enterprise level database tracking reports and presentations for the enterprise client of individual and group level results.

4. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 14:
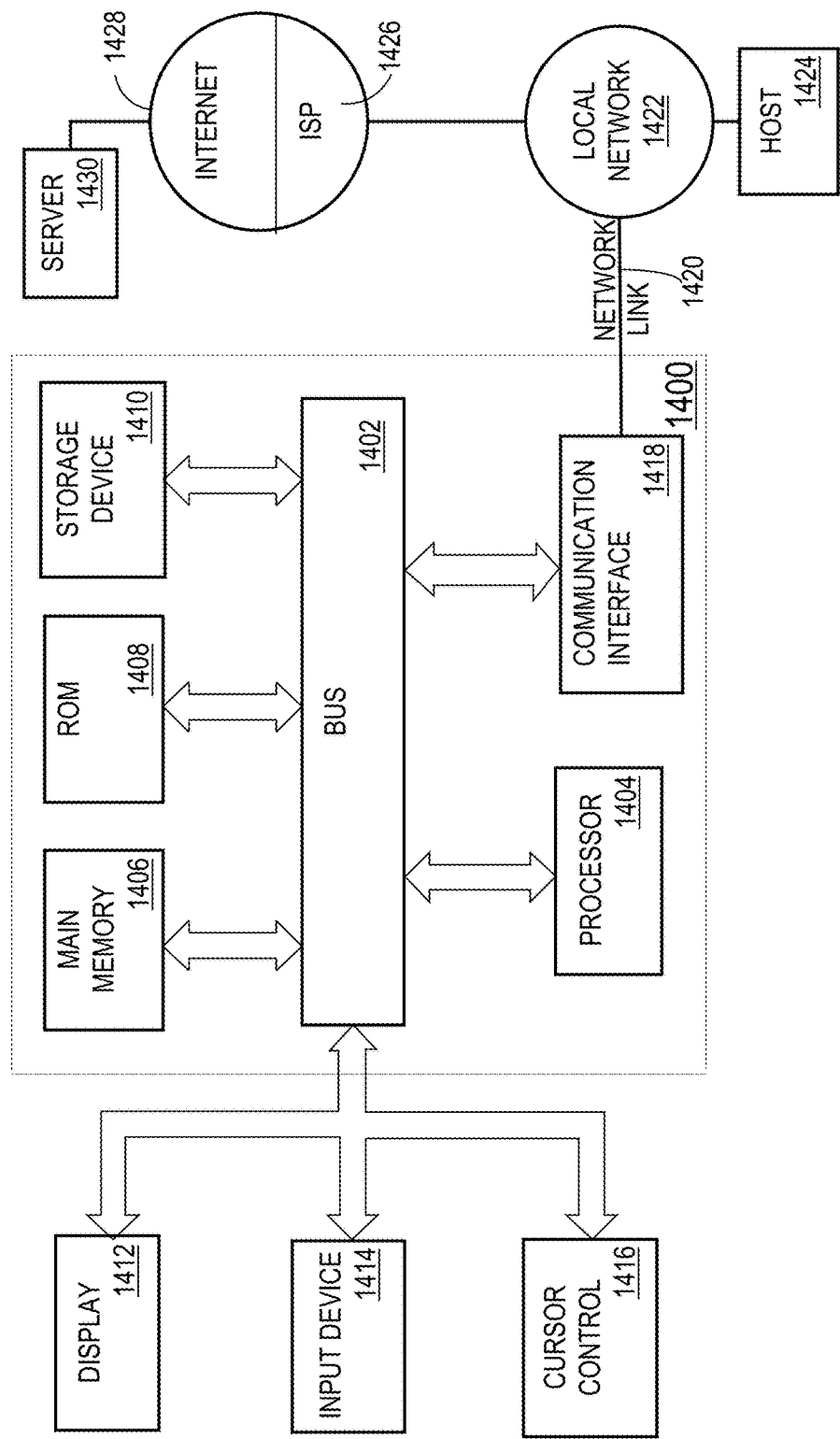
FIG. 14 is a block diagram that illustrates a computer system upon which an embodiment of the invention may be implemented.

For example, FIG. 14 is a block diagram that illustrates a computer system 1400 upon which an embodiment of the invention may be implemented. Computer system 1400 includes a bus 1402 or other communication mechanism for communicating information, and a hardware processor 1404 coupled with bus 1402 for processing information. Hardware processor 1404 may be, for example, a general purpose microprocessor.

Computer system 1400 also includes a main memory 1406, such as a random access memory (RAM) or other dynamic storage device, coupled to bus 1402 for storing information and instructions to be executed by processor 1404. Main memory 1406 also may be used for storing temporary variables or other intermediate information during execution of instructions to be executed by processor 1404. Such instructions, when stored in non-transitory storage media accessible to processor 1404, render computer system 1400 into a special-purpose machine that is customized to perform the operations specified in the instructions.

Computer system 1400 further includes a read only memory (ROM) 1408 or other static storage device coupled to bus 1402 for storing static information and instructions for processor 1404. A storage device 1410, such as a magnetic disk, optical disk, or solid-state drive is provided and coupled to bus 1402 for storing information and instructions.

Computer system 1400 may be coupled via bus 1402 to a display 1412, such as a cathode ray tube (CRT), for displaying information to a computer user. An input device 1414, including alphanumeric and other keys, is coupled to bus 1402 for communicating information and command selections to processor 1404. Another type of user input device is cursor control 1416, such as a mouse, a trackball, or cursor direction keys for communicating direction information and command selections to processor 1404 and for controlling cursor movement on display 1412. This input device typically has two degrees of freedom in two axes, a first axis (e.g., x) and a second axis (e.g., y), that allows the device to specify positions in a plane.

Computer system 1400 may implement the techniques described herein using customized hard-wired logic, one or more ASICs or FPGAs, firmware and/or program logic which in combination with the computer system causes or programs computer system 1400 to be a special-purpose machine. According to one embodiment, the techniques herein are performed by computer system 1400 in response to processor 1404 executing one or more sequences of one or more instructions contained in main memory 1406. Such instructions may be read into main memory 1406 from another storage medium, such as storage device 1410. Execution of the sequences of instructions contained in main memory 1406 causes processor 1404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 1410. Volatile media includes dynamic memory, such as main memory 1406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1402. Transmission media can also take the form of acoustic or light waves, such as those generated during radio-wave and infra-red data communications.

Various forms of media may be involved in carrying one or more sequences of one or more instructions to processor 1404 for execution. For example, the instructions may initially be carried on a magnetic disk or solid-state drive of a remote computer. The remote computer can load the instructions into its dynamic memory and send the instructions over a telephone line using a modem. A modem local to computer system 1400 can receive the data on the telephone line and use an infra-red transmitter to convert the data to an infra-red signal. An infra-red detector can receive the data carried in the infra-red signal and appropriate circuitry can place the data on bus 1402. Bus 1402 carries the data to main memory 1406, from which processor 1404 retrieves and executes the instructions. The instructions received by main memory 1406 may optionally be stored on storage device 1410 either before or after execution by processor 1404.

Computer system 1400 also includes a communication interface 1418 coupled to bus 1402. Communication interface 1418 provides a two-way data communication coupling to a network link 1420 that is connected to a local network 1422. For example, communication interface 1418 may be an integrated services digital network (ISDN) card, cable modem, satellite modem, or a modem to provide a data communication connection to a corresponding type of telephone line. As another example, communication interface 1418 may be a local area network (LAN) card to provide a data communication connection to a compatible LAN. Wireless links may also be implemented. In any such implementation, communication interface 1418 sends and receives electrical, electromagnetic or optical signals that carry digital data streams representing various types of information.

Network link 1420 typically provides data communication through one or more networks to other data devices. For example, network link 1420 may provide a connection through local network 1422 to a host computer 1424 or to data equipment operated by an Internet Service Provider (ISP) 1426. ISP 1426 in turn provides data communication services through the world wide packet data communication network now commonly referred to as the "Internet" 1428. Local network 1422 and Internet 1428 both use electrical, electromagnetic or optical signals that carry digital data streams. The signals through the various networks and the signals on network link 1420 and through communication interface 1418, which carry the digital data to and from computer system 1400, are example forms of transmission media.

Computer system 1400 can send messages and receive data, including program code, through the network(s), network link 1420 and communication interface 1418. In the Internet example, a server 1430 might transmit a requested code for an application program through Internet 1428, ISP 1426, local network 1422 and communication interface 1418.

The received code may be executed by processor 1404 as it is received, and/or stored in storage device 1410, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A data processing method comprising:
   loading a mobile computing device with test instructions upon startup of an application installed on the mobile computing device;
   under program control of the test instructions programmed in the mobile computing device, generating and causing displaying on a display device of the mobile computing device, a prompt associated with a first task relating to a test of a feature of a human cognitive domain, wherein the prompt comprises a prompt image of spatially positioned shapes and lines;
   in conjunction with causing displaying the prompt, by the test instructions, reading a system clock of the mobile computing device and storing a first time stamp value indicating when the prompt was displayed;
   wherein the system clock continuously generates signals representing a current time that may be queried programmatically by the application;
   using the test instructions, displaying the prompt for a specified time period using the system clock;
   in response to displaying the prompt for the specified time period, causing displaying a graphical grid that is configured to capture movement input at the mobile computing device wherein the movement input comprises drawing or placing shapes and lines to recreate the prompt image;
   by the test instructions, obtaining input via the grid displayed through the mobile computing device comprising a response to the prompt, wherein the response comprises the movement input of shapes, icons, characters, or lines;
   in conjunction with obtaining the input, by the test instructions, reading the system clock of the mobile computing device and storing a second time stamp value indicating when the input comprising the response was detected, and storing, in association with the second time stamp value, a tag indicating the movement input for the response;
   by the test instructions, repeating the generating and causing displaying, the obtaining, the storing the tag, and the storing the first time stamp value and the second time stamp value, for a plurality of other prompts of other tasks relating to the same test or the same first task, to yield a plurality of test records that associate a plurality of different response values with a plurality of respective different time stamp values, and transmitting the plurality of different response values and the plurality of respective different time stamp values over a data communications network to a server computer that is programmed with test analysis instructions;
   by the test analysis instructions, based upon the plurality of different response values and the plurality of respective different time stamp values, determining a first result score value for the first task, applying a first weight value to the first result score value to yield a first weighted result score value, and combining one or more other different weighted result score values associated with the other prompts of the other tasks relating to the same test, or the same first task, with the first weighted result score value to yield a cognitive domain score value;
   with the server computer, causing generating and displaying one or more different graphs of the features of the cognitive domain, including a brain profile type;
   further comprising, with the server computer, causing generating and displaying the one or more different graphs of the features of the cognitive domain, including the brain profile type, in which the different weighted result score values are indicated as positions within a normal distribution of score values for those features.

2. The method of claim 1, wherein the test instructions are further programmed:
   to execute a verbal learning task having an instant verbal learning test and a delayed verbal learning test, and one or more stroop tests;
   to combine a first weighted result score value of the instant verbal learning test with a second weighted result score value of the delayed verbal learning test to yield the cognitive domain score value for a verbal memory domain; and to combine the first weighted result score value of the instant verbal learning test with the second weighted result score value of the delayed verbal learning test and with a third weighted result score value of the one or more stroop tests to yield a second cognitive domain score value for a verbal processing speed domain.

3. The method of claim 1, wherein the test instructions are further programmed:

to execute a digit span task, a maze task, a figure copy task, and a trail test;

to combine a first weighted result score value of the digit span task with a second weighted result score value of the maze task to yield the cognitive domain score value for a working memory domain;

to combine the second weighted result score value of the maze task with a third weighted result score value of the figure copy task to yield a second cognitive domain score value for a spatial memory domain;

to combine the second weighted result score value of the maze task with the third weighted result score value of the figure copy task and a fourth weighted result score value of the trail test to yield a third cognitive domain score value for a spatial processing speed domain.

4. The method of claim 1, wherein the test instructions are further programmed to execute a verbal learning task.

5. The method of claim 1, wherein the test instructions are further programmed to execute a color word task.

6. The method of claim 1, wherein the test instructions are programmed to execute a complex figure task.

7. The method of claim 1, wherein the test instructions are further programmed to execute an emotional recognition task.

8. The method of claim 1, wherein the test instructions are further programmed to execute a gambling task.

9. The method of claim 1, wherein the test instructions are further programmed to execute a maze task.

10. The method of claim 1, wherein the test instructions are further programmed to execute an N-back task.

11. The method of claim 1, wherein the test instructions are further programmed to execute a trail task.

12. The method of claim 1, wherein the first time stamp value and the second time stamp value include a millisecond value.

13. The method of claim 1, wherein the test instructions are programmed to execute a test battery consisting of a verbal learning task, a color word task, a complex figure task, an emotional recognition task, a gambling task, a maze task, an N-back task, and a trail task, in any order, and to store a plurality of response values and time stamp values for each response and the time of each response for a plurality of different responses to different prompts as part of all tasks in the test battery, and wherein each of the time stamp values include a millisecond value.

14. The method of claim 1, wherein the test instructions are programmed to obtain touch input via a touch screen display of the mobile computing device comprising the response to the prompt.

15. A data processing method comprising:

downloading, from a server computer to a mobile computing device, a test application comprising a plurality of sequences of test instructions, which when executed using the mobile computing device cause the mobile computing device to perform:

loading the mobile computing device with test instructions upon startup of an application installed on the mobile computing device;

generating and causing displaying on a display device of the mobile computing device, under program control of test instructions, a prompt associated with a first task relating to a test of a feature of a human cognitive domain, wherein the prompt comprises a prompt image of spatially positioned shapes and lines;

in conjunction with causing displaying the prompt, by the test instructions, reading a system clock of the mobile computing device and storing a first time stamp value indicating when the prompt was displayed;

wherein the system clock continuously generates signals representing a current time that may be queried programmatically by the application;

using the test instructions, displaying the prompt for a specified time period using the system clock;

in response to displaying the prompt for the specified time period, causing displaying a graphical grid that is configured to capture movement input at the mobile computing device wherein the movement input comprises drawing or placing shapes and lines to recreate the prompt image;

by the test instructions, obtaining input via the grid displayed through the mobile computing device comprising a response to the prompt, wherein the response comprises the movement input of shapes, icons, characters, or lines;

in conjunction with obtaining the input, by the test instructions, reading the system clock of the mobile computing device and storing a second time stamp value indicating when the input comprising the response was detected, and storing, in association with the second time stamp value, a tag indicating the movement input for the response;

by the test instructions, repeating the generating and causing displaying, the obtaining, the storing the tag, and the storing the first time stamp value and the second time stamp value, for a plurality of other prompts of other tasks relating to the same test or the same first task to yield a plurality of test records that associate a plurality of different response values with a plurality of respective different time stamp values, and transmitting the plurality of different response values and the plurality of respective different time stamp values over a data communications network to the server computer;

at the server computer, based upon the plurality of different response values and the plurality of respective different time stamp values, determining a first result score value for the first task, applying a first weight value to the first result score value to yield a first weighted result score value, and combining one or more other different weighted result score values associated with the other prompts of the other tasks relating to the same test, or the same first task, with the first weighted result score value to yield a cognitive domain score value;

with the server computer, causing generating a web page displaying one or more different graphs of the features of the cognitive domain, including a brain profile type, and transmitting the web page to a client computer;

further comprising, with the server computer, causing generating and displaying the one or more different graphs of the features of the cognitive domain, including the brain profile type, in which the different weighted result score values are indicated as positions within a normal distribution of score values for those features.

16. The method of claim 15, wherein the test instructions are further programmed when executed by the mobile computing device:
- to execute a verbal learning task having an instant verbal learning test and a delayed verbal learning test, and one or more stroop tests;
- to combine a first weighted result score value of the instant verbal learning test with a second weighted result score value of the delayed verbal learning test to yield the cognitive domain score value for a verbal memory domain; and
- to combine the first weighted result score value of the instant verbal learning test with the second weighted result score value of the delayed verbal learning test and with a third weighted result score value of the one or more stroop tests to yield a second cognitive domain score value for a verbal processing speed domain.

17. The method of claim 15, wherein the test instructions are further programmed when executed by the mobile computing device:
- to execute a digit span task, a maze task, a figure copy task, and a trail test;
- to combine a first weighted result score value of the digit span task with a second weighted result score value of the maze task to yield the cognitive domain score value for a working memory domain;
- to combine the second weighted result score value of the maze task with a third weighted result score value of the figure copy task to yield a second cognitive domain score value for a spatial memory domain;
- to combine the second weighted result score value of the maze task with the third weighted result score value of the figure copy task and a fourth weighted result score value of the trail test to yield a third cognitive domain score value for a spatial processing speed domain.

18. The method of claim 15, wherein the first time stamp value and the second time stamp value include a millisecond value.

19. The method of claim 15, wherein the test instructions are programmed to cause the mobile computing device to execute a test battery consisting of a verbal learning task, a color word task, a complex figure task, an emotional recognition task, a gambling task, a maze task, an N-back task, and a trail task, in any order, and to store a plurality of response values and time stamp values for each response and the time of each response for a plurality of different responses to different prompts as part of all tasks in the test battery, and wherein each of the time stamp values include a millisecond value.

* * * * *